United States Patent [19]
Kato et al.

[11] Patent Number: 5,902,469
[45] Date of Patent: May 11, 1999

[54] GAS SENSOR

[75] Inventors: Nobuhide Kato, Ama-gun; Kunihiko Nakagaki, Nagoya, both of Japan

[73] Assignee: NGK Insulators, Ltd., Japan

[21] Appl. No.: 08/820,351

[22] Filed: Mar. 12, 1997

[30] Foreign Application Priority Data

Mar. 21, 1996 [JP] Japan ................................... 8-064650
Feb. 25, 1997 [JP] Japan ................................... 9-040829

[51] Int. Cl.⁶ ................................................. G01N 27/41
[52] U.S. Cl. ................................ 204/425; 204/426
[58] Field of Search ................................ 204/421–429

[56] References Cited

U.S. PATENT DOCUMENTS

| | | | |
|---|---|---|---|
| 4,770,760 | 9/1988 | Noda et al. | 204/425 |
| 4,824,549 | 4/1989 | Hamada et al. | 204/410 |
| 4,927,517 | 5/1990 | Mizutani et al. | 204/425 |
| 5,034,112 | 7/1991 | Murase et al. | 204/425 |
| 5,098,549 | 3/1992 | Friese et al. | 204/424 |
| 5,145,566 | 9/1992 | Logothetis et al. | 204/424 |
| 5,304,294 | 4/1994 | Wang et al. | 204/424 |
| 5,476,001 | 12/1995 | Hoetzel et al. | 73/23.31 |
| 5,643,429 | 7/1997 | Wachman | 204/425 |
| 5,672,811 | 9/1997 | Kato et al. | 204/427 |

FOREIGN PATENT DOCUMENTS

| | | |
|---|---|---|
| 0 678 740 A1 | 10/1995 | European Pat. Off. . |
| 731351 A2 | 9/1996 | European Pat. Off. . |
| WO 95/30146 | 11/1995 | WIPO . |

*Primary Examiner*—T. Tung
*Attorney, Agent, or Firm*—Parkhurst & Wendel

[57] ABSTRACT

Disclosed is a gas sensor comprising inner pumping electrodes arranged on upper and lower surfaces and both side surfaces in a first chamber so that $O_2$ contained in a measurement gas introduced through a first diffusion rate-determining section is effectively removed by the aid of a pumping voltage applied between the inner pumping electrodes and an outer pumping electrode. After the removal of $O_2$, the measurement gas is introduced into a second chamber through a second diffusion rate-determining section so that oxides contained in the measurement gas are decomposed by the aid of a detecting electrode, or $O_2$ is bound to inflammable gases contained in the measurement gas. An amount of oxygen moved or transported in accordance therewith is measured to determine the concentration of the oxides or the inflammable gases. Accordingly, the oxygen contained in the measurement gas can be effectively controlled, making it possible to highly accurately measure the oxides or the inflammable gases.

13 Claims, 12 Drawing Sheets

GAS SENSOR

BACKGROUND OF THE INVENTION

1. Field of the Invention

The present invention relates to a gas sensor for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm. In particular, the present invention relates to a gas sensor for measuring NO and $NO_2$.

2. Description of the Related Art

Exhaust gas, which is discharged, for example, from vehicles or automobiles such as gasoline-fueled automobiles and diesel powered automobiles, contains nitrogen oxides (NOx) such as nitrogen monoxide (NO) and nitrogen dioxide ($NO_2$), as well as carbon monoxide (CO), carbon dioxide ($CO_2$), water ($H_2O$), hydrocarbon (HC), hydrogen ($H_2$), oxygen ($O_2$) and so on. In such exhaust gas, about 80% of the entire NOx is occupied by NO, and about 95% of the entire NOx is occupied by NO and $NO_2$.

The three way catalyst, which is used to clean HC, CO, and NOx contained in the exhaust gas, exhibits its maximum cleaning efficiency in the vicinity of the theoretical air fuel ratio (A/F=14.6). If A/F is controlled to be not less than 16, the amount of produced NOx is decreased. However, the cleaning efficiency of the catalyst is lowered, and consequently the amount of discharged NOx is apt to increase.

Recently, in order to effectively utilize fossil fuel and avoid global warming, the market demand increases, for example, in that the discharge amount of $CO_2$ should be suppressed. In order to respond to such a demand, it becomes more necessary to improve the fuel efficiency. In response to such a demand, for example, the lean burn engine and the catalyst for cleaning NOx are being researched. Especially, the need for a NOx sensor increases.

A conventional NOx analyzer has been hitherto known as an instrument for detecting NOx. The conventional NOx analyzer is operated to measure a characteristic inherent in NOx, based on the use of chemical luminous analysis. However, the conventional NOx analyzer is inconvenient in that the instrument itself is extremely large and expensive. The conventional NOx analyzer requires frequent maintenance because optical parts are used to detect NOx. Further, when the conventional NOx analyzer is used, any sampling operation should be performed for measurement of NOx, where it is impossible to directly insert a detecting element itself into a fluid. Therefore, the conventional NOx analyzer is not suitable for analyzing transient phenomena such as those occur in the exhaust gas discharged from an automobile, in which the condition frequently varies.

In order to dissolve the inconveniences as described above, there has been already suggested a sensor for measuring a desired gas component in exhaust gas by using a substrate comprising an oxygen ion-conductive solid electrolyte.

FIG. 14 shows a system of a gas analyzer disclosed in International Publication WO 95/30146. This apparatus comprises a first chamber 4 into which a measurement gas G containing NO is introduced through a narrow hole 2, and a second chamber 8 into which the measurement gas G is introduced from the first chamber 4 through a narrow hole 6. Wall surfaces for constructing the first and second chambers 4, 8 are composed of partition walls 10a, 10b made of zirconia ($ZrO_2$) capable of transmitting oxygen ion. A pair of measuring electrodes 12a, 12b and a pair of measuring electrodes 14a, 14b for measuring the partial pressure of oxygen in the respective chambers are arranged on portions of one $ZrO_2$ partition wall 10a corresponding to the first and second chambers 4, 8 respectively. A set of pumping electrodes 16a, 16b and a set of pumping electrodes 18a, 18b for pumping out $O_2$ in the respective chambers to the outside of the chambers are arranged on the other $ZrO_2$ partition wall 10b.

The gas analyzer thus constructed functions as follows. Namely, the partial pressure of oxygen contained in the measurement gas G introduced into the first chamber 4 through the narrow hole 2 is detected by a voltmeter 20 as an electric potential difference generated between the measuring electrodes 12a, 12b. A voltage of 100 to 200 mV is applied between the pumping electrodes 16a, 16b by the aid of a power source 22 so that the electric potential difference is adjusted to have a predetermined value. Accordingly, $O_2$ in the first chamber 4 is pumped out to the outside of the apparatus. The amount of pumped out oxygen can be measured by using an ammeter 24.

The measurement gas G, from which almost all $O_2$ has been removed, is introduced into the second chamber 8 through the narrow hole 6. In the second chamber 8, an electric potential difference generated between the measuring electrodes 14a, 14b is detected by a voltmeter 26. Thus the partial pressure of oxygen in the second chamber 8 is measured. On the other hand, NO contained in the measurement gas G introduced into the second chamber 8 is decomposed as follows by the aid of a voltage applied between the pumping electrodes 18a, 18b by means of a power source 28:

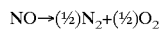

$O_2$ produced by the decomposition is pumped out to the outside of the second chamber 8 by the aid of the pumping electrodes 18a, 18b. A value of an electric current generated during this process is detected by an ammeter 30. Thus the concentration of NO contained in the measurement gas G is measured.

However, in the case of the gas analyzer constructed as described above, if the concentration of oxygen contained in the measurement gas G is high, $O_2$ in the first chamber 4 cannot be sufficiently pumped out to the outside of the chamber 4 by the aid of the pumping electrodes 16a, 16b. As a result, unprocessed $O_2$ enters the second chamber 8 together with NO. Therefore, an error due to $O_2$ occurs in the current value obtained by decomposition of NO.

Namely, as shown in FIG. 15, the pumping electrode 16b in the first chamber 4 is arranged only on one $ZrO_2$ partition wall 10b. Therefore, the oxygen concentration in the first chamber 4 is apt to increase in accordance with increase in separating distance from the pumping electrode 16b, as illustrated by a characteristic curve a. On the other hand, as illustrated by a characteristic curve b, the oxygen concentration in the widthwise direction in the first chamber 4 is apt to have a maximum at a position corresponding to the narrow hole 2 through which the measurement gas G is introduced. Therefore, a part of the measurement gas G introduced into the first chamber 4 through the narrow hole 2, especially a part of the measurement gas G passing through a central portion of the first chamber 4 in the vicinity of the measuring electrode 12b is introduced into the second chamber 8 through the narrow hole 6 without being affected by the pumping electrode 16b. As a result, $O_2$ is excessively introduced, and hence an error occurs in the measured value of NO due to the influence of excessively introduced $O_2$.

SUMMARY OF THE INVENTION

The present invention has been made in order to overcome the inconvenience described above, an object of which is to provide a gas sensor which makes it possible to effectively control the amount of oxygen contained in a measurement gas, and thus measure the amount of oxides or inflammable gases contained in the measurement gas with an extremely high degree of accuracy.

In order to achieve the object described above, the present invention provides a gas sensor comprising a main pumping means including inner and outer pumping electrodes arranged on inner and outer surfaces of a substrate composed of an oxygen ion-conductive solid electrolyte, for performing a pumping process for oxygen contained in a measurement gas introduced from external space, on the basis of a control voltage applied between the inner and outer pumping electrodes; and an electric signal-generating conversion means including inner and outer detecting electrodes arranged on inner and outer surfaces of a substrate composed of an oxygen ion-conductive solid electrolyte, for decomposing a predetermined gas component contained in the measurement gas after being subjected to the pumping process performed by the main pumping means, by the aid of a catalytic action and/or electrolysis to provide, by conversion, an electric signal corresponding to an amount of oxygen produced by the decomposition; wherein the main pumping means includes a plurality of the inner pumping electrodes which are arranged on at least upper and lower surfaces of a process space processed by the main pumping means, and the predetermined gas component contained in the measurement gas is measured on the basis of the electric signal supplied from the electric signal-generating conversion means.

According to the present invention, at first, the oxygen in the measurement gas introduced from the external space is subjected to the pumping process performed by the main pumping means, and the oxygen is adjusted to have a predetermined concentration. The measurement gas, in which the oxygen concentration has been adjusted by the main pumping means, is introduced into the electric signal-generating conversion means in the next step. The electric signal-generating conversion means serves to decompose the predetermined gas component contained in the measurement gas after being subjected to the pumping process performed by the main pumping means, by the aid of the catalytic action and/or electrolysis, and provide, by conversion, the electric signal corresponding to the amount of oxygen produced by the decomposition. After that, the predetermined gas component contained in the measurement gas is measured on the basis of the electric signal supplied from the electric signal-generating conversion means.

The gas sensor may comprise a measuring pumping means and a current-detecting means to serve as the electric signal-generating conversion means. In this preferred embodiment, the measurement gas, in which the oxygen concentration has been adjusted by the main pumping means, is introduced into the measuring pumping means.

In the measuring pumping means, the predetermined gas component contained in the measurement gas after being subjected to the pumping process performed by the main pumping means is decomposed by the aid of the catalytic action and/or electrolysis. The oxygen produced by the decomposition is subjected to a pumping process performed by the measuring pumping means on the basis of a measuring voltage applied between inner and outer detecting electrodes. A pumping current is generated in the measuring pumping means, corresponding to an amount of oxygen subjected to the pumping process performed by the measuring pumping means. The generated pumping current is detected by the current-detecting means. Thus the predetermined gas component is measured, corresponding to the amount of oxygen.

In another preferred embodiment, the gas sensor of the present invention may comprise a concentration-detecting means and a voltage-detecting means to serve as the electric signal-generating conversion means. In this embodiment, the measurement gas, in which the concentration of oxygen has been adjusted by the main pumping means, is introduced into the concentration-detecting means in the next step. In the concentration-detecting means, the predetermined gas component contained in the measurement gas after being subjected to the pumping process performed by the main pumping means is decomposed by the aid of the catalytic action and/or electrolysis. The concentration-detecting means generates an electromotive force of an oxygen concentration cell, corresponding to a difference between an amount of oxygen produced by the decomposition and an amount of oxygen contained in a gas existing on a side of an outer detecting electrode. The generated electromotive force is detected by the voltage-detecting means. Thus the predetermined gas component is measured, corresponding to the amount of oxygen.

In the gas sensor according to the present invention, the main pumping means includes the inner pumping electrodes arranged at least on the upper and lower surfaces of the process space processed by the main pumping means. Accordingly, the oxygen in the process space processed by the main pumping means can be effectively pumped out to the external space. As a result, the predetermined gas component contained in the measurement gas can be measured with a high degree of accuracy by the aid of the measuring pumping means and the current-detecting means, or by the aid of the concentration-detecting means and the voltage-detecting means.

Oxides in the measurement gas, for example, nitrogen oxides can be measured highly accurately by using the gas sensor according to the present invention. When the atmosphere in the process space processed by the main pumping means is set to have a predetermined amount of oxygen with which no inflammable gas burns, it is also possible to highly accurately measure inflammable gases, for example, gas components such as hydrogen, carbon monoxide, and hydrocarbon.

In the gas sensor constructed as described above, it is preferable that the inner pumping electrodes are arranged on the upper and lower surfaces and at least one of side surfaces of the process space processed by the main pumping means, and the arranged inner pumping electrodes are electrically connected to one another. In this embodiment, the main pumping means can more effectively pump out oxygen from the process space processed by the main pumping means.

The gas sensor constructed as described above may further comprise a plurality of process spaces each having a diffusion rate-determining section for giving a predetermined diffusion resistance to the measurement gas, for measuring different types of oxides or inflammable gases respectively.

In this embodiment, for example, a plurality of process spaces (referred to as "second chambers" for convenience) processed by the measuring pumping means or the concentration-detecting means, which are linked to the process space (referred to as "first chamber" for convenience)

processed by the main pumping means, may be arranged in series or in parallel to the first chamber. Thus a plurality of oxides of different types can be measured by using one sensor in each of the second chambers by individually setting the pumping voltage applied between the electrodes of the measuring pumping means, corresponding to each of the measurement-objective oxides, or by individually setting a decomposing catalyst arranged in the measuring pumping means or the concentration-detecting means, corresponding to each of the measurement-objective oxides.

It is also preferable for the gas sensor constructed as described above that the inner pumping electrodes may be composed of an inactive material having a low catalytic activity on oxides. In this embodiment, the oxide-decomposing reaction on the inner pumping electrodes is suppressed more appropriately. Thus the oxides can be measured with a higher degree of accuracy by the aid of the measuring pumping means or the concentration-detecting means.

In the gas sensor constructed as described above, the control voltage supplied to the main pumping means may be set to be a voltage at which the partial pressure of oxygen in the process space processed by the main pumping means is not less than $2 \times 10^{-8}$ atm. Accordingly, the measurement gas, which is adjusted to have a desired oxygen concentration, is supplied to the process space processed by the measuring pumping means or the process space processed by the concentration-detecting means.

The gas sensor constructed as described above may further comprise an auxiliary pumping means including inner and outer auxiliary pumping electrodes arranged on inner and outer surfaces of a substrate composed of an oxygen ion-conductive solid electrolyte, for performing a pumping process for oxygen contained in the measurement gas after being subjected to the pumping process performed by the main pumping means, on the basis of an auxiliary pumping voltage applied between the inner and outer auxiliary pumping electrodes.

Accordingly, the measurement gas, which has been firstly subjected to the coarse adjustment so that the predetermined gas component has a predetermined concentration by the aid of the main pumping means, is further subjected to the fine adjustment for the concentration of the predetermined gas component by the aid of the auxiliary pumping means.

In general, when the concentration of the predetermined gas component in the measurement gas in the external space greatly changes (for example, from 0 to 20%), the concentration distribution of the predetermined gas component in the measurement gas introduced into the main pumping means greatly changes. The amount of the predetermined gas component introduced into the measuring pumping means or the concentration-detecting means also changes.

In such a situation, the oxygen concentration in the measurement gas after being subjected to the pumping process performed by the main pumping means is finely adjusted upon the pumping process performed by the auxiliary pumping means. Significantly, the change in oxygen concentration in the measurement gas introduced into the auxiliary pumping means is greatly reduced as a result of the pumping process performed by the main pumping means, as compared with the change in oxygen concentration in the measurement gas supplied from the external space (the measurement gas introduced into the main pumping means). Accordingly, the concentration of the predetermined gas component can be accurately and constantly controlled in the vicinity of the inner detecting electrode of the measuring pumping means or in the vicinity of the outer detecting electrode of the concentration-detecting means.

Therefore, the concentration of the predetermined gas component introduced into the measuring pumping means or the concentration-detecting means is scarcely affected by the change in oxygen concentration in the measurement gas (the measurement gas introduced into the main pumping means). As a result, the pumping current value detected by the current-detecting means or the electromotive force detected by the voltage-detecting means is not affected by the change in concentration of oxygen in the measurement gas. Thus a value is obtained, which accurately corresponds to the amount of the objective component existing in the measurement gas.

In particular, the auxiliary pumping means includes a plurality of the inner auxiliary pumping electrodes arranged at least on upper and lower surfaces of the process space processed by the auxiliary pumping means. Accordingly, it is possible to efficiently remove excessive oxygen contained in the measurement gas introduced into the auxiliary pumping means. Thus the objective gas components contained in the measurement gas can be measured with a higher degree of accuracy.

The gas sensor constructed as described above may further comprise a concentration-detecting means including an inner measuring electrode exposed to the process space processed by the main pumping means and an outer measuring electrode exposed to a reference gas-introducing space, for measuring an electromotive force of an oxygen concentration cell generated between the inner and outer measuring electrodes, as a partial pressure of oxygen in the process space processed by the main pumping means; and a main pumping control means for adjusting a level of the control voltage so that the electromotive force of the oxygen concentration cell detected by the concentration-measuring means has a predetermined value.

Accordingly, the electromotive force is generated in the concentration-measuring means, corresponding to the difference between the amount of oxygen contained in the measurement gas during the pumping process performed by the main pumping means and the amount of oxygen contained in the gas existing on the side of the outer measuring electrode. The level of the control voltage applied between the inner and outer pumping electrodes of the main pumping means is adjusted on the basis of the electromotive force by the aid of the main pumping control means.

The main pumping means performs the pumping process for an amount of the oxygen in the measurement gas introduced from the external space, the amount corresponding to the level of the control voltage. The oxygen concentration in the measurement gas is subjected to feedback control so that the oxygen concentration is at a predetermined level by supplying, to the main pumping means, the control voltage having been subjected to the adjustment for the level as described above.

Especially, the gas sensor according to the present invention can measure nitrogen oxides such as NO and $NO_2$ with a high degree of accuracy.

It is preferable that each of the substrates for constructing each of the process spaces is heated to a predetermined temperature by using a heating means in order to give desired characteristics of oxygen ion conductivity. In this embodiment, it is preferable that the electrodes arranged in the process space processed by the measuring pumping means or the concentration-detecting means are arranged on the substrate located on a side of the heating means.

A means for giving a predetermined diffusion resistance to the measurement gas (referred to as "first diffusion rate-determining section" for convenience) may be arranged between the external space and the process space processed by the main pumping means. Further, a means for giving a predetermined diffusion resistance to the measurement gas (referred to as "second diffusion rate-determining section" for convenience) may be arranged between the process space processed by the main pumping means and the process space processed by the measuring pumping means or the concentration-detecting means. In this embodiment, it is desirable that the diffusion resistance of the second diffusion rate-determining section is set to be larger than the diffusion resistance of the first diffusion rate-determining section.

It is preferable to use an Rh cermet as the oxide-decomposing catalyst arranged in the process space processed by the measuring pumping means or the concentration-detecting means. The oxide-decomposing catalyst may be provided as the electrode. Alternatively, the oxide-decomposing catalyst may be provided as a catalyst layer separately from the electrode.

In the gas sensor according to the present invention, the outer detecting electrode is arranged at a position exposed to a space into which the reference gas is introduced. Thus the oxygen produced by the decomposition of the predetermined gas component can be compared with the oxygen contained in the reference gas, making it possible to detect the predetermined gas component more accurately.

Especially, it is preferable that the outer detecting electrode is combined into a common unit with the outer auxiliary pumping electrode and the outer measuring electrode. In this embodiment, a common electrode, which serves as the outer detecting electrode of the measuring pumping means or the concentration-detecting means, the outer auxiliary pumping electrode of the auxiliary pumping means, and the outer measuring electrode of the concentration-measuring means, is exposed to the reference gas-introducing space. The common electrode can be defined as a reference electrode for the respective detecting processes performed by the measuring pumping means, the concentration-detecting means, and the concentration-measuring means. In accordance with this definition, the inner detecting electrode of the measuring pumping means and the concentration-detecting means can be defined as a detecting electrode, the inner auxiliary pumping electrode of the auxiliary pumping means can be defined as an auxiliary electrode, and the inner measuring electrode of the concentration-measuring means can be defined as a measuring electrode.

According to the present invention, the amount of inflammable gases contained in the measurement gas can be measured highly accurately on the basis of a pumping current corresponding to an amount of oxygen pumped into the process space processed by the measuring pumping means or the concentration-detecting means to be bound by the inflammable gases. In this embodiment, the control voltage set for the main pumping means is established so that the electromotive force of the oxygen concentration cell is, for example, 930 mV. Thus it is possible to supply the measurement gas in which no inflammable gas burns, to the process space processed by the measuring pumping means or the concentration-detecting means.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Several illustrative embodiments, in which the gas sensor according to the present invention is applied to gas sensors for measuring oxides such as $NO$, $NO_2$, $SO_2$, $CO_2$, and $H_2O$, and inflammable gases such as $CO$ and $CnHm$ contained in, for example, atmospheric air and exhaust gas discharged from vehicles or automobiles, will be explained below with reference to FIGS. 1 to 13.

Figure 1:
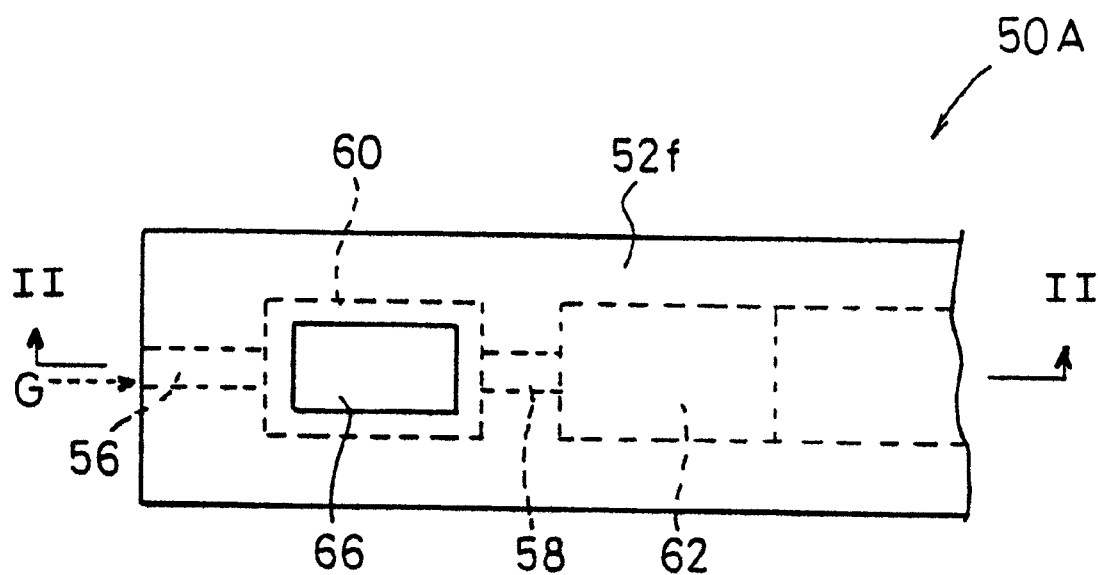
FIG. 1 shows a plan view illustrating a gas sensor according to a first embodiment.
Figure 2:
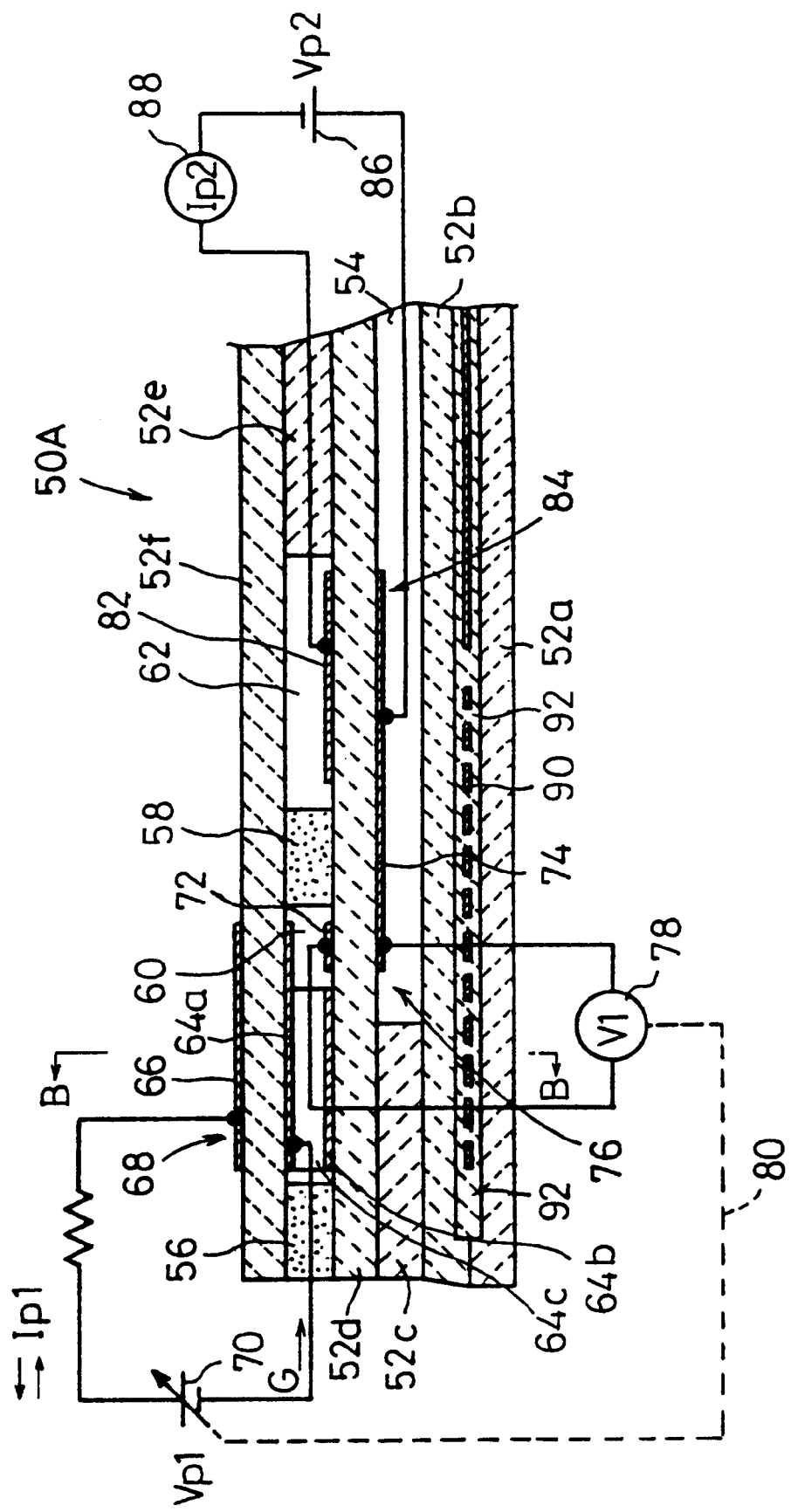
FIG. 2 shows a cross-sectional view taken along a line A—A in FIG. 1.

At first, as shown in FIGS. 1 and 2, a gas sensor 50A according to a first embodiment has a lengthy plate-shaped configuration as a whole, comprising, for example, six stack solid electrolyte layers 52a to 52f composed of ceramics based on the use of oxygen ion-conductive solid electrolytes such as $ZrO_2$. First and second layers from the bottom are designated as first and second substrate layers 52a, 52b respectively. Third and fifth layers from the bottom are designated as first and second spacer layers 52c, 52e respectively. Fourth and sixth layers from the bottom are designated as first and second solid electrolyte layers 52d, 52f respectively.

Specifically, the first spacer layer 52c is stacked on the second substrate layer 52b. The first solid electrolyte layer 52d, the second spacer layer 52e, and the second solid electrolyte layer 52f are successively stacked on the first spacer layer 52c.

A space (reference gas-introducing space 54), into which a reference gas such as atmospheric air to be used as a reference for measuring oxides is introduced, is formed between the second substrate layer 52b and the first solid electrolyte layer 52d, the space being comparted by a lower surface of the first solid electrolyte layer 52d, an upper surface of the second substrate layer 52b, and a side surface of the first spacer layer 52c.

The second spacer layer 52e is interposed between the first and second solid electrolyte layers 52d, 52f. First and second diffusion rate-determining sections 56, 58 are also interposed between the first and second solid electrolyte layers 52d, 52f.

A first chamber 60 for adjusting the partial pressure of oxygen in a measurement gas G is formed and comparted by a lower surface of the second solid electrolyte layer 52f, side surfaces of the first and second diffusion rate-determining sections 56, 58, and an upper surface of the first solid electrolyte layer 52d. A second chamber 62 for finely adjusting the partial pressure of oxygen in the measurement gas G and measuring oxides, for example, nitrogen oxides (NOx) in the measurement gas G is formed and comparted by a lower surface of the second solid electrolyte layer 52f, a side surface of the second diffusion rate-determining section 58, a side surface of the second spacer layer 52e, and an upper surface of the first solid electrolyte layer 52d.

The external space communicates with the first chamber 60 through the first diffusion-rate determining section 56, and the first chamber 60 communicates with the second chamber 62 through the second diffusion rate-determining section 58.

The first and second diffusion-rate determining sections 56, 58 give predetermined diffusion resistances to the measurement gas G to be introduced into the first and second chambers 60, 62 respectively. Each of the first and second diffusion-rate determining sections 56, 58 can be formed as a passage composed of, for example, a porous material, or a small hole having a predetermined cross-sectional area so that the measurement gas G may be introduced.

Especially, the second diffusion-rate determining section 58 is arranged and filled with a porous material comprising, for example, $ZrO_2$. The diffusion resistance of the second diffusion-rate determining section 58 is made larger than the diffusion resistance of the first diffusion-rate determining section 56.

The gas sensor 50A according to the first embodiment includes inner pumping electrodes 64a to 64d composed of porous cermet electrodes formed on inner wall surfaces of the first chamber 60. An outer pumping electrode 66 is formed on a portion corresponding to the inner pumping electrode 64a, of the upper surface of the second solid electrolyte layer 52f. An electrochemical pumping cell, i.e., a main pumping cell 68 is constructed by the inner pumping electrodes 64a to 64d, the outer pumping electrode 66, the second solid electrolyte layer 52f interposed between the both electrodes 64, 66, the first solid electrolyte layer 52d, and the second spacer layer 52e.

Figure 3:
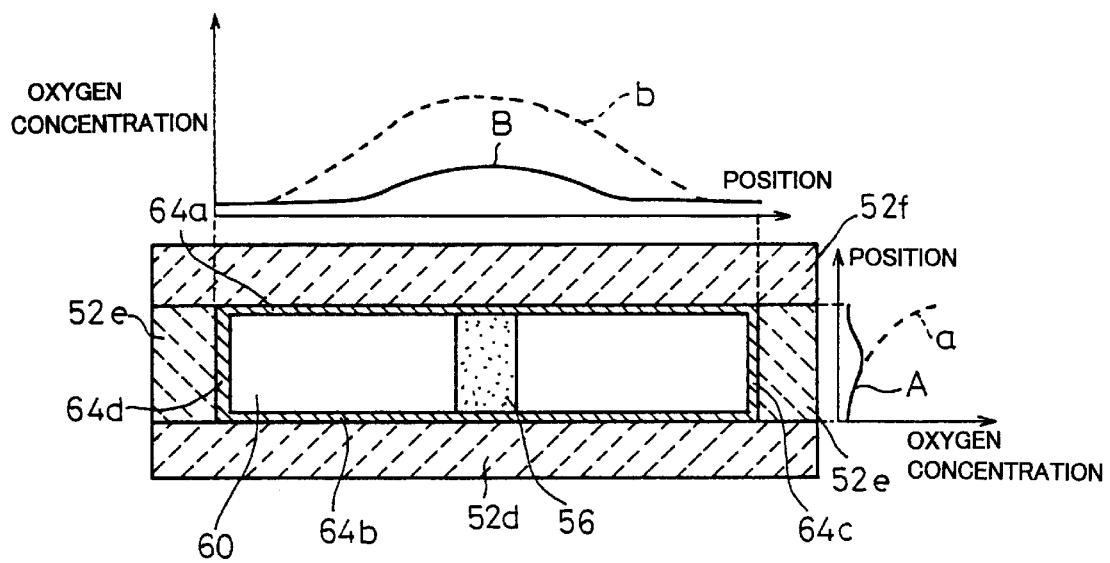
FIG. 3 shows a cross-sectional view taken along a line B—B in FIG. 2, together with an illustration of the distribution of oxygen concentration in a first chamber.

As shown in FIG. 3, the inner pumping electrodes 64a to 64d are continuous to one another so that the inner wall surfaces of the first chamber 60 is surrounded by them. The inner pumping electrode 64a is arranged on the lower surface of the second solid electrolyte layer 52f which is the upper surface of the wall for constructing the first chamber 60. The inner pumping electrode 64b is arranged on the upper surface of the first solid electrolyte layer 52d which is the lower surface of the wall. The inner pumping electrodes 64c, 64d are arranged on the side surfaces of the spacer layer 52e which provides the side surfaces of the wall. The inner pumping electrodes 64a, 64b, 64c, 64d are continuously formed and constructed.

It is allowable for the inner pumping electrodes 64a to 64d to use only one of the inner pumping electrode 64a arranged on the upper surface and the inner pumping electrode 64b arranged on the lower surface. Alternatively, it is allowable for the inner pumping electrodes 64a to 64d to use three electrodes of the inner pumping electrodes 64a, 64b arranged on both the upper and lower surfaces, and any one of the pumping electrodes 64c, 64d arranged on the side surfaces.

A desired control voltage (pumping voltage) Vp1 is applied between the inner pumping electrodes 64a to 64d and the outer pumping electrode 66 of the main pumping cell 68 by the aid of an external variable power source 70 to allow a pumping current Ip1 to flow in a positive or negative direction between the outer pumping electrode 66 and the inner pumping electrodes 64a to 64d. Thus the oxygen in the atmosphere in the first chamber 60 can be pumped out to the external space, or the oxygen in the external space can be pumped into the first chamber 60.

A measuring electrode 72, which is composed of a porous cermet electrode having a flat and substantially rectangular shape, is formed on a portion (on which the inner pumping electrode 64b is not formed) adjacent to the second diffusion rate-determining section 58, of the upper surface of the first solid electrolyte layer 52d for forming the first chamber 60. A reference electrode 74 is formed on a portion exposed to the reference gas-introducing space 54, of the lower surface of the first solid electrolyte layer 52d. An electrochemical sensor cell, i.e., a controlling oxygen partial pressure-detecting cell 76 is constructed by the measuring electrode 72, the reference electrode 74, and the first solid electrolyte layer 52d.

An electromotive force is generated between the measuring electrode 72 and the reference electrode 74 of the controlling oxygen partial pressure-detecting cell 76 on the basis of a difference in oxygen concentration between the atmosphere in the first chamber 60 and the reference gas (atmospheric air) in the reference gas-introducing space 54. The partial pressure of oxygen in the atmosphere in the first chamber 60 can be detected by measuring the generated electromotive force by the aid of a voltmeter 78.

Namely, the voltage V1, which is generated between the reference electrode 74 and the measuring electrode 72, is an electromotive force of the oxygen concentration cell, generated on the basis of a difference between a partial pressure of oxygen in the reference gas introduced into the reference gas-introducing space 54 and a partial pressure of oxygen in the measurement gas G in the first chamber 60. The voltage V1 has the following relationship known as the Nernst's equation.

$$V1 = RT/4F \cdot \ln(P1(O_2)/P0(O_2))$$

R: gas constant;

T: absolute temperature;

F: Faraday constant;

$P1(O_2)$: partial pressure of oxygen in the first chamber 60;

$P0(O_2)$: partial pressure of oxygen in the reference gas. Therefore, the partial pressure of oxygen in the first chamber 60 can be detected by measuring the voltage V1 generated on the basis of the Nernst's equation, by the aid of the voltmeter 78.

The detected value of the partial pressure of oxygen is used to control the pumping voltage of the variable power source 70 by the aid of a feedback control system 80. Specifically, the pumping operation performed by the main pumping cell 68 is controlled so that the partial pressure of oxygen in the first chamber 60 has a predetermined value which is sufficiently low to control the partial pressure of oxygen in the second chamber 62 in the next step.

The inner pumping electrodes 64a to 64d and the outer pumping electrode 66 are composed of an inactive material having a low catalytic activity on NOx, for example, NO in the measurement gas G introduced into the first chamber 60. Specifically, the inner pumping electrodes 64a to 64d and the outer pumping electrode 66 can be composed of a porous cermet electrode. In this embodiment, they are formed of a metal such as Pt and a ceramic such as $ZrO_2$. Especially, it is necessary, for the inner pumping electrodes 64a to 64d and the measuring electrode 72 arranged in the first chamber 60 contacting with the measurement gas G, to use a material having a weak reducing ability or no reducing ability with respect to the NO components in the measurement gas. It is preferable that the inner pumping electrodes 64a to 64d and the measuring electrode 72 are composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

The gas sensor 50A according to the first embodiment includes a detecting electrode 82 composed of a porous cermet electrode having a flat and substantially rectangular shape. The detecting electrode 82 is formed on a portion separated from the second diffusion rate-determining section 58, of the upper surface of the first solid electrolyte layer 52d for forming the second chamber 62. An electrochemical pumping cell, i.e., a measuring pumping cell 84 is constructed by the detecting electrode 82, the reference electrode 74, and the first solid electrolyte layer 52d.

The detecting electrode 82 can be constructed by appropriately selecting a nitrogen oxide-decomposing catalyst, for example, an Rh cermet, a material having a low catalytic activity, or a combination of a nitrogen oxide-decomposing catalyst arranged in the vicinity of a material having a low catalytic activity. In this embodiment, the detecting electrode 82 is composed of a porous cermet comprising Rh as a metal capable of reducing NOx as the objective gas component, and zirconia as a ceramic.

Accordingly, NOx existing in the measurement gas G introduced into the second chamber 62 is decomposed by the catalytic action exerted by the detecting electrode 82. A constant voltage Vp2 at a level, at which $O_2$ produced from NOx decomposed by the detecting electrode 82 can be sufficiently pumped out toward the reference gas-introducing space 54, is applied between the detecting electrode 82 and the reference electrode 74 by the aid of a DC power source 86. The DC power source 86 can apply a voltage having a magnitude sufficient to give a limiting current to the pumping for oxygen produced during the decomposition in the measuring pumping cell 84.

Thus a pumping current Ip2 is allowed to flow through the measuring pumping cell 84, corresponding to an amount of oxygen pumped out by the pumping operation performed by the measuring pumping cell 84. The pumping current Ip2 is detected by an ammeter 88.

A pumping voltage sufficient to decompose NOx may be applied between the detecting electrode 82 and the reference electrode 74. Alternatively, an oxide-decomposing catalyst for decomposing NOx may be arranged in the second chamber 62. Thus $O_2$ produced by the action of the pumping voltage and/or the oxide-decomposing catalyst may be pumped out from the second chamber 62 at a predetermined pumping voltage.

As shown in FIG. 2, the gas sensor 50A according to the first embodiment includes a heater 90 for generating heat in accordance with electric power supply from the outside. The heater 90 is embedded in a form of being vertically interposed between the first and second substrate layers 52a, 52b. The heater 90 is provided in order to increase the conductivity of oxygen ion. A ceramic layer 92 composed of alumina or the like is formed to cover upper and lower surfaces of the heater 90 so that the heater 90 is electrically insulated from the first and second substrate layers 52a, 52b.

The heater 90 is arranged to extend over an entire region ranging from the first chamber 60 to the second chamber 62. Thus the first and second chambers 60, 62 are heated to predetermined temperatures respectively. Further, the main pumping cell 68, the controlling oxygen partial pressure-detecting cell 76, and the measuring pumping cell 84 are also heated to and maintained at predetermined temperatures respectively.

The gas sensor 50A according to the first embodiment is basically constructed as described above. Next, its function and effect will be explained.

Before the measurement of oxides, the gas sensor 50A is set in a state in which the measurement gas G can be introduced into the first chamber 60. Next, an electric power is applied to the heater 90 so that the first and second solid electrolyte layers 52d, 52f are activated to have desired states.

Next, the measurement of oxides contained in the measurement gas G is started by introducing the measurement gas G into the gas sensor 50A having been set as described above.

The measurement gas G is introduced into the first chamber 60 under a predetermined diffusion resistance through the first diffusion rate-determining section 56. The partial pressure of oxygen contained in the measurement gas G is controlled to have a predetermined value in accordance with a predetermined pumping voltage Vp1 applied between the inner pumping electrodes 64a to 64d and the outer pumping electrode 66 by the aid of the variable power source 70.

Namely, the partial pressure of oxygen in the first chamber 60 can be measured on the basis of a voltage V1 between the reference electrode 74 and the measuring electrode 72, detected by the voltmeter 78. The voltage V1 is an electromotive force of the oxygen concentration cell defined by the Nernst's equation described above. The pumping voltage Vp1 applied by the variable power source 70 is controlled by the aid of the feedback control system 80 so that the voltage V1 is, for example, not more than 350 mV (not less than $1.2 \times 10^{-8}$ atm expressed as a converted value into the partial pressure of oxygen). Thus the partial pressure of oxygen in the first chamber 60 is controlled to have a predetermined value.

The measurement gas G, which has been controlled to have the predetermined partial pressure of oxygen in the first chamber 60, is introduced into the second chamber 62 through the second diffusion rate-determining section 58 designed to have a diffusion resistance larger than that of the first diffusion rate-determining section 56.

Oxides contained in the measurement gas G introduced into the second chamber 62 are decomposed by a predetermined measuring pumping voltage Vp2 applied by the DC power source 86 between the reference electrode 74 and the detecting electrode 82, or by the oxide-decomposing catalyst arranged in the second chamber 62. $O_2$ thus produced is pumped out toward the reference gas-introducing space 54 through the first solid electrolyte layer 52d. In this process, a current value Ip2, which is generated by movement of oxygen ion, is measured by the ammeter 88. The concentration of predetermined oxides, for example, NOx such as NO and $NO_2$ contained in the measurement gas G is determined from the current value Ip2.

Especially, the gas sensor 50A according to the first embodiment includes, in the first chamber 60, the inner pumping electrodes 64a to 64d which are arranged to surround the passage of the measurement gas G introduced into the first chamber 60. Accordingly, the concentration of $O_2$ contained in the measurement gas G can be controlled extremely effectively.

Namely, as shown in FIG. 3, the inner pumping electrodes 64a, 64b are arranged on the upper and lower surfaces in the first chamber 60. Accordingly, $O_2$ in the measurement gas G introduced through the first diffusion rate-determining section 56 is ionized and pumped out to the outside by the aid of the both inner pumping electrodes 64a, 64b.

Therefore, as for the vertical direction in the first chamber 60, the oxygen concentration is controlled to be low regardless of the vertical position as represented by a characteristic curve A, as compared with a conventional characteristic curve a. As for the widthwise direction, the oxygen concentration is slightly increased at a central portion corresponding to the passage of the measurement gas G as represented by a characteristic curve B, however, the fluctuation of oxygen concentration in the widthwise direction is greatly suppressed, as compared with a conventional characteristic curve b. Since the inner pumping electrodes 64c, 64d are also arranged on the side surfaces in the first chamber 60, it is possible to control the oxygen concentration more effectively.

Figure 14:
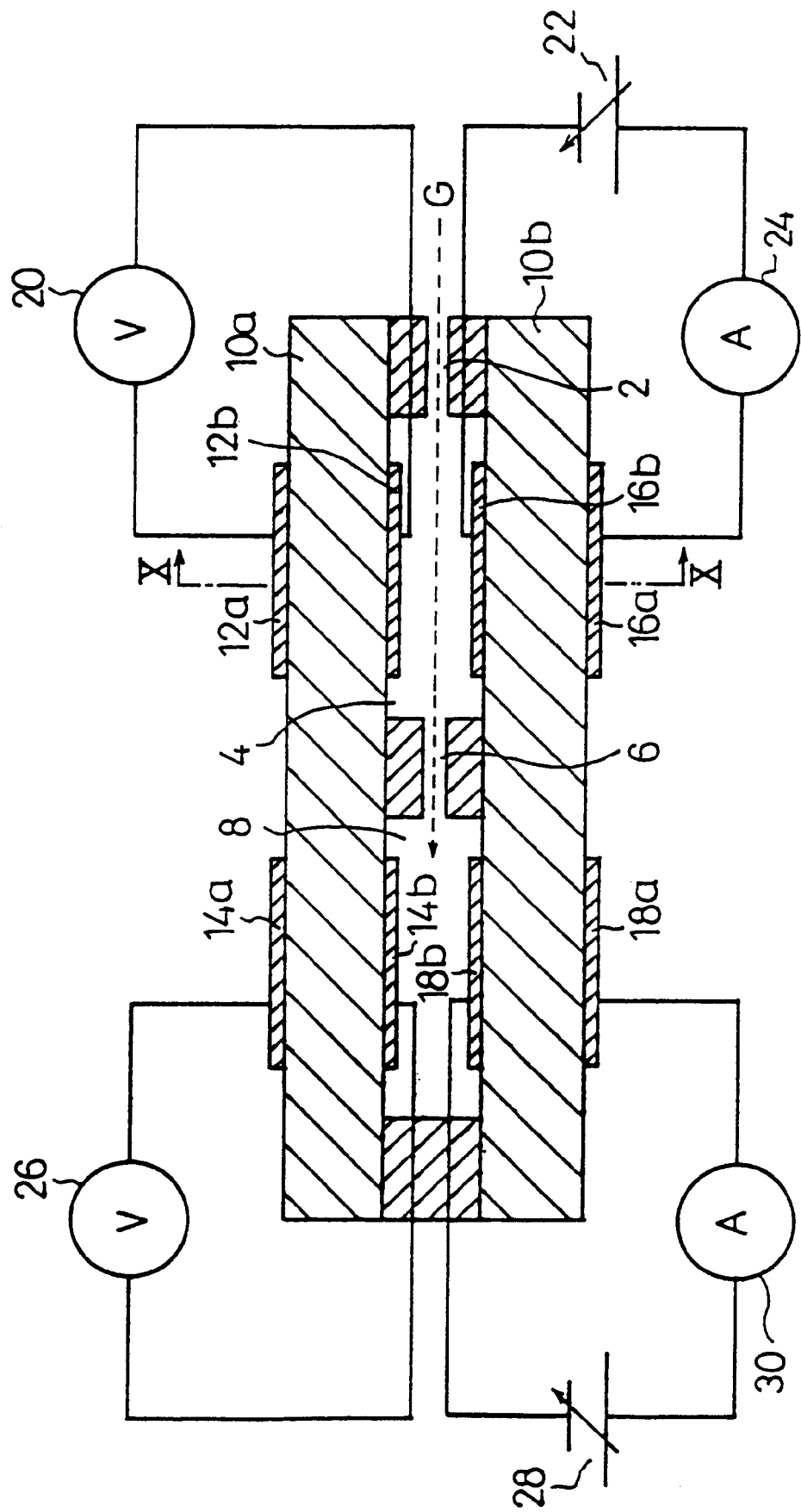
FIG. 14 shows a cross-sectional view illustrating a system of a gas analyzer concerning the conventional technique.
Figure 15:
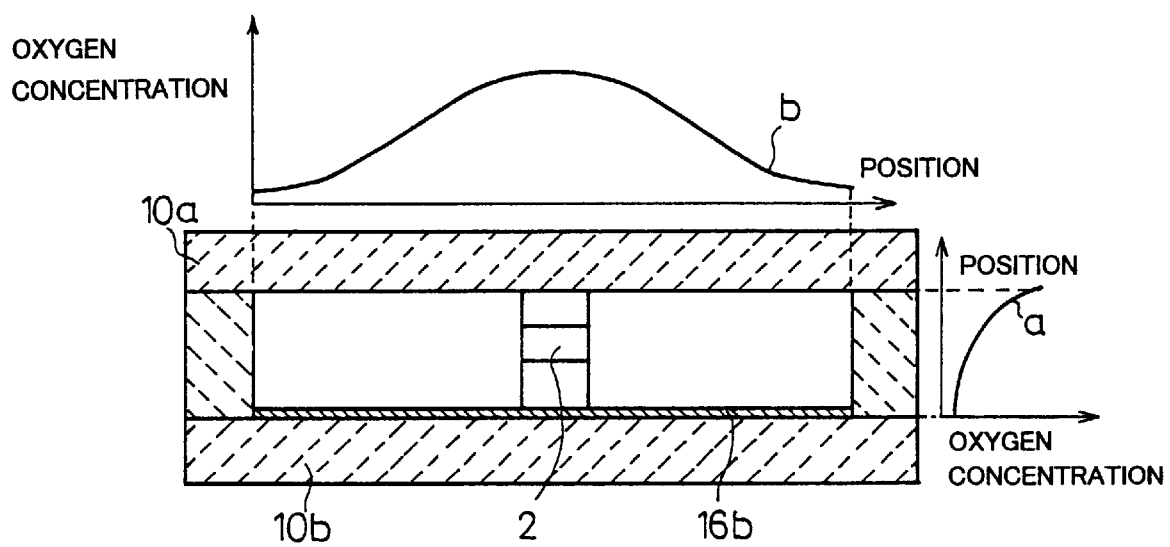
FIG. 15 shows a cross-sectional view taken along a line X—X in FIG. 14, together with an illustration of the distribution of oxygen concentration in a first chamber.

Now two illustrative experiments will be described. The illustrative experiments were performed by providing Example 1 and Comparative Example. Example 1 was based on the use of a system constructed in the same manner as the gas sensor 50A according to the first embodiment including the inner pumping electrodes 64a to 64d formed on the inner wall surfaces of the first chamber 60. Comparative Example was based on the use of a system constructed in the same manner as the gas sensor concerning the conventional technique as shown in FIG. 14.

Figure 4:
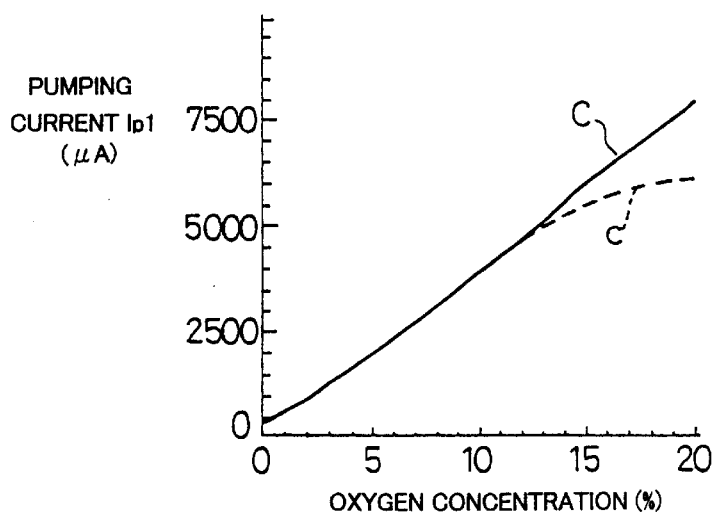
FIG. 4 shows experimental results obtained in a first illustrative experiment, representing characteristic curves concerning the relationship between the oxygen concentration in a measurement gas and the pumping current Ip1 flowing through a main pumping cell.

In the first illustrative experiment, observation was made for the relationship between the oxygen concentration (%) contained in the measurement gas G and the pumping current Ip1 ($\mu$A) generated by pumping out $O_2$ between the inner pumping electrodes 64a to 64d and the outer pumping electrode 66, concerning Example 1 and Comparative Example. Experimental results obtained in the first illustrative experiment are shown in FIG. 4. In FIG. 4, a characteristic curve C indicated by a solid line represents an experimental result obtained in Example 1, and a characteristic curve c indicated by a broken line represents an experimental result obtained in Comparative Example.

According to the experimental results shown in FIG. 4, the characteristic curve C obtained in Example 1 is linear in a range of oxygen concentration of 0 to 20%, owing to the enlarged area of the inner pumping electrodes 64a to 64d, as compared with the characteristic curve c obtained in Comparative Example. According to this fact, it is understood that the oxygen concentration can be easily controlled in Example 1 over a broad range of $O_2$ concentration contained in the measurement gas G.

Figure 5:
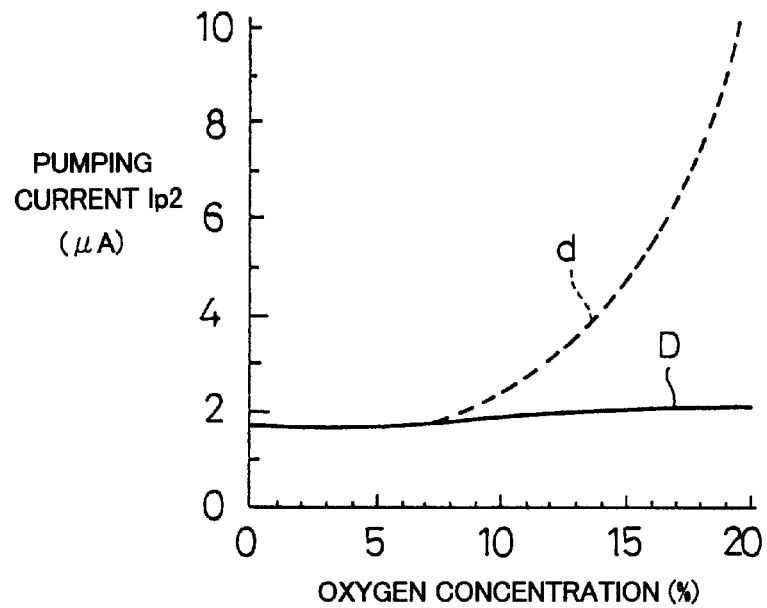
FIG. 5 shows experimental results obtained in a second illustrative experiment, representing characteristic curves concerning the relationship between the oxygen concentration in a measurement gas and the pumping current Ip2 flowing through a measuring pumping cell.

In the second illustrative experiment, demonstration was made for the relationship between the oxygen concentration (%) contained in the measurement gas G and the pumping current Ip2 ($\mu$A) generated by decomposition of NOx between the detecting electrode 82 and the reference electrode 74, concerning Example 1 and Comparative Example. Experimental results obtained in the second illustrative experiment are shown in FIG. 5. In FIG. 5, a characteristic curve D indicated by a solid line represents an experimental result obtained in Example 1, and a characteristic curve d indicated by a broken line represents an experimental result obtained in Comparative Example.

According to the experimental results shown in FIG. 5, the characteristic curve D obtained in Example 1 provides a constant pumping current Ip2 irrelevant to the oxygen concentration contained in the measurement gas G, as compared with the characteristic curve d obtained in Comparative Example. This fact demonstrates that the measurement of NOx in the second chamber 62 suffers no influence, because $O_2$ contained in the measurement gas G is sufficiently pumped out in the first chamber 60 by the aid of the inner pumping electrodes 64a to 64d.

According to the results described above, $O_2$ contained in the measurement gas G can be removed extremely effectively by enlarging the area of the inner pumping electrode 64a to 64d of the main pumping cell 68 so that the passage for the measurement gas G is surrounded by the inner pumping electrodes 64a to 64d arranged on the inner wall surfaces of the first chamber 60. Therefore, it is possible to highly accurately measure the amount of oxides contained in the measurement gas G introduced into the second chamber 62, without being affected by $O_2$.

The gas sensor 50A according to the first embodiment has been explained in a form in which only one second chamber 62 is linked to the first chamber 60. However, it is also allowable to provide a plurality of the second chambers 62 connected to the first chamber 60 so that a plurality of oxides of different types may be simultaneously measured. For example, a third chamber constructed in the same manner as the second chamber 62 is provided and connected in series to the second chamber 62 through a diffusion rate-determining section. Further, a pumping voltage, which is different from the pumping voltage applied to the detecting electrode 82 for the second chamber 62, is applied to an electrode for the third chamber. Thus it is possible to measure oxides of a type different from those measured in the second chamber 62. The oxides include, for example, NO, $NO_2$, $CO_2$, $H_2O$, and $SO_2$. It is also possible to connect the third chamber to the second chamber 62 in parallel.

The gas sensor 50A according to the first embodiment can be also applied as a sensor for highly accurately measuring the amount of inflammable gases such as CO and hydrocarbon contained in the measurement gas G.

In such application of the gas sensor 50A according to the first embodiment, the pumping voltage Vp1 is controlled to give an electromotive force V1 of, for example, 930 mV generated by the controlling oxygen partial pressure-detecting cell 76, between the inner pumping electrodes 64a to 64d and the outer pumping electrode 66 of the main pumping cell 68. Accordingly, the oxygen concentration in the first chamber 60 is adjusted to be a concentration at which no inflammable gas burns.

Next, the measurement gas G is introduced into the second chamber 62. In the second chamber 62, the measuring pumping voltage Vp2 of the DC power source 86 is controlled so that the electromotive force of the oxygen concentration cell is 450 mV. It is noted that no oxide-decomposing catalyst is arranged in the second chamber 62.

Thus the inflammable gas in the measurement gas G introduced into the second chamber 62 is bound to $O_2$ pumped into the second chamber 62 from the outside by the aid of the measuring pumping voltage Vp2 applied to the detecting electrode 82. Thus the amount of the inflammable gas can be measured by detecting the pumping current Ip2 flowing through the ammeter 88.

Figure 6:
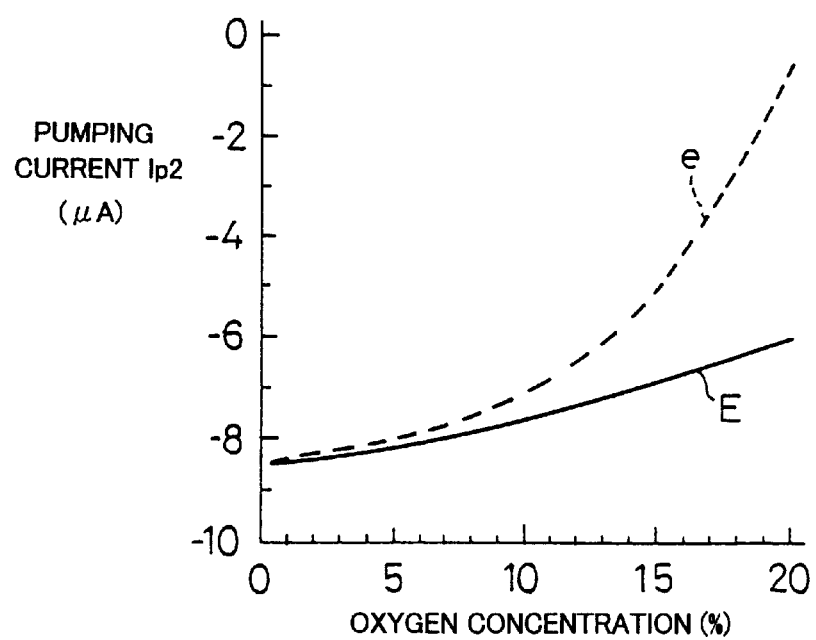
FIG. 6 shows experimental results obtained in a third illustrative experiment, representing characteristic curves concerning the relationship between the oxygen concentration in a measurement gas and the pumping current Ip2 flowing through a measuring pumping cell.

Now, an illustrative experiment (referred to as "third illustrative experiment" for convenience) will be described. In the third illustrative experiment, observation was made for the relationship between the oxygen concentration (%) contained in the measurement gas G and the pumping current Ip2 ($\mu$A) generated by binding of $O_2$ and the inflammable gas, between the detecting electrode 82 and the reference electrode 74, concerning Example 1 and Comparative Example. Experimental results obtained in the third illustrative experiment are shown in FIG. 6. In FIG. 6, a characteristic curve E indicated by a solid line represents an experimental result obtained in Example 1, and a characteristic curve e indicated by a broken line represents an experimental result obtained in Comparative Example.

According to the experimental results shown in FIG. 6, the characteristic curve E obtained in Example 1 provides a substantially constant pumping current irrelevant to the oxygen concentration contained in the measurement gas G, as compared with the characteristic curve e obtained in Comparative Example. This fact demonstrates that the measurement of the inflammable gas in the second chamber 62 suffers no influence, because $O_2$ contained in the measurement gas G is sufficiently pumped out by the aid of the inner pumping electrodes 64a to 64d in the first chamber 60.

Next, a gas sensor 50B according to a second embodiment will be explained with reference to FIG. 7. Components or parts of the gas sensor 50B corresponding to those shown in FIG. 2 are designated by the same reference numerals, duplicate explanation of which will be omitted.

Figure 7:
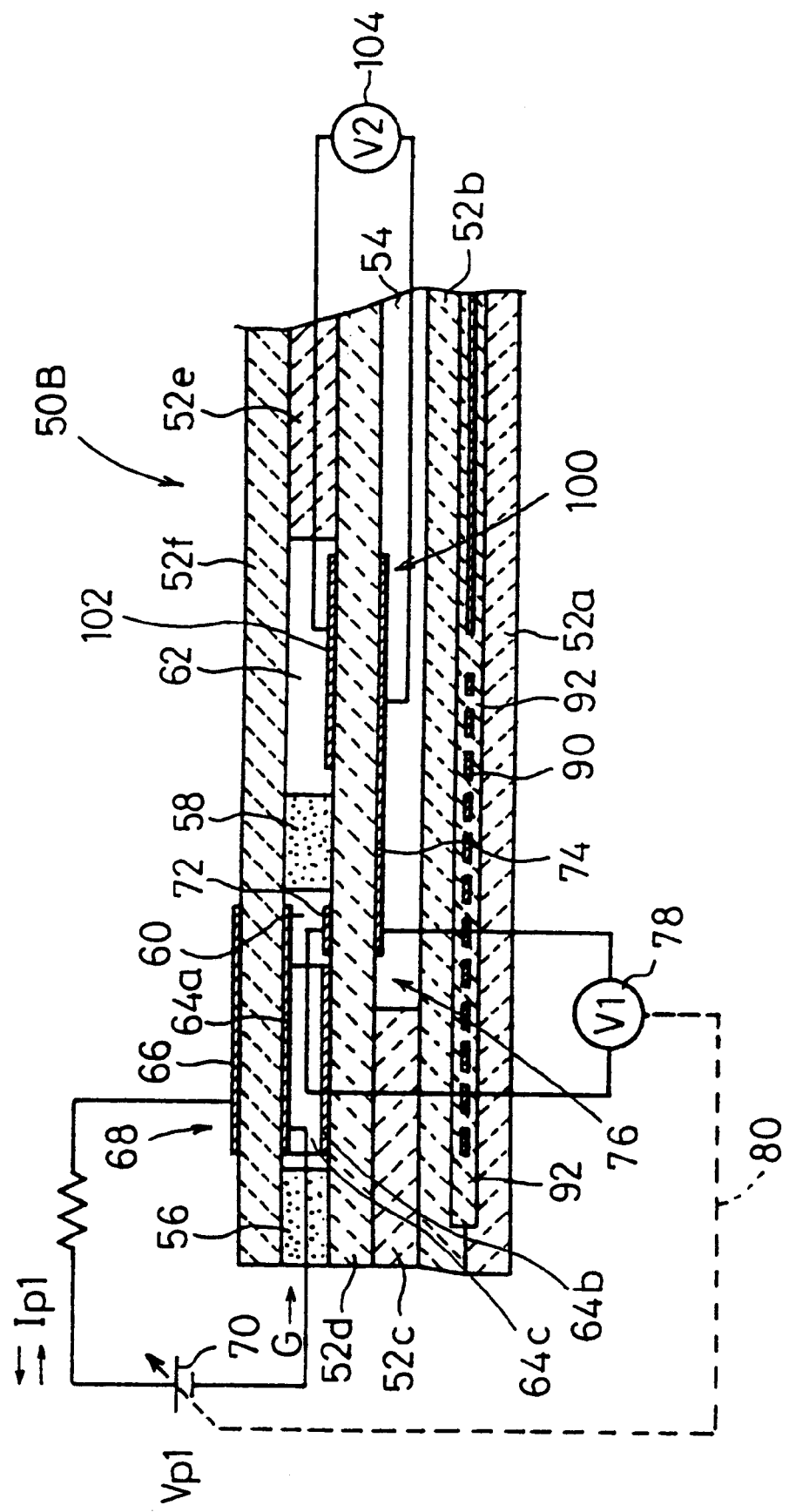
FIG. 7 shows a cross-sectional view illustrating a gas sensor according to a second embodiment.

As shown in FIG. 7, the gas sensor 50B according to the second embodiment has approximately the same structure as that of the gas sensor 50A according to the first embodiment (see FIG. 2). However, the former is different from the latter in that a measuring oxygen partial pressure-detecting cell 100 is provided in place of the measuring pumping cell 84.

The measuring oxygen partial pressure-detecting cell 100 comprises a detecting electrode 102 formed on a portion for forming the second chamber 62, of the upper surface of the first solid electrolyte layer 52d, the reference electrode 74 formed on the lower surface of the first solid electrolyte layer 52d, and the first solid electrolyte layer 52d.

In this embodiment, an electromotive force (electromotive force of an oxygen concentration cell) V2 is generated between the detecting electrode 102 and the reference electrode 74 of the measuring oxygen partial pressure-detecting cell 100, corresponding to a difference in oxygen concentration between an atmosphere around the detecting electrode 102 and an atmosphere around the reference electrode 74.

Therefore, the partial pressure of oxygen in the atmosphere around the detecting electrode 102, in other words, the partial pressure of oxygen defined by oxygen produced by reduction or decomposition of the measurement gas components (NOx) is detected as a value of the voltage V2 by measuring the electromotive force (voltage) V2 generated between the detecting electrode 102 and the reference electrode 74 by using a voltmeter 104.

The degree of change in electromotive force V2 represents the NOx concentration. Namely, the electromotive force V2, which is outputted from the measuring oxygen partial pressure-detecting cell 100 constructed by the detecting electrode 102, the reference electrode 74, and the first solid electrolyte layer 52d, represents the NOx concentration in the measurement gas G.

In the gas sensor 50B according to the second embodiment, the inner pumping electrodes 64a to 64d are arranged to surround the passage for the measurement gas G introduced into the first chamber 60. Accordingly, it is possible to extremely effectively control the concentration of $O_2$ contained in the measurement gas G. Thus it is possible to highly accurately measure NOx including NO and $NO_2$ by using the gas sensor 50B.

Now, two illustrative experiments (referred to as "fourth and fifth illustrative experiments" respectively) will be described. The illustrative experiments were performed by providing Example 2 and Comparative Example. Example 2 was based on the use of a system constructed in the same manner as the gas sensor 50B according to the second embodiment including the inner pumping electrodes 64a to 64d formed on the inner wall surfaces of the first chamber 60. Comparative Example was based on the use of a system constructed in the same manner as the gas sensor concerning the conventional technique as shown in FIG. 14.

Figure 8:
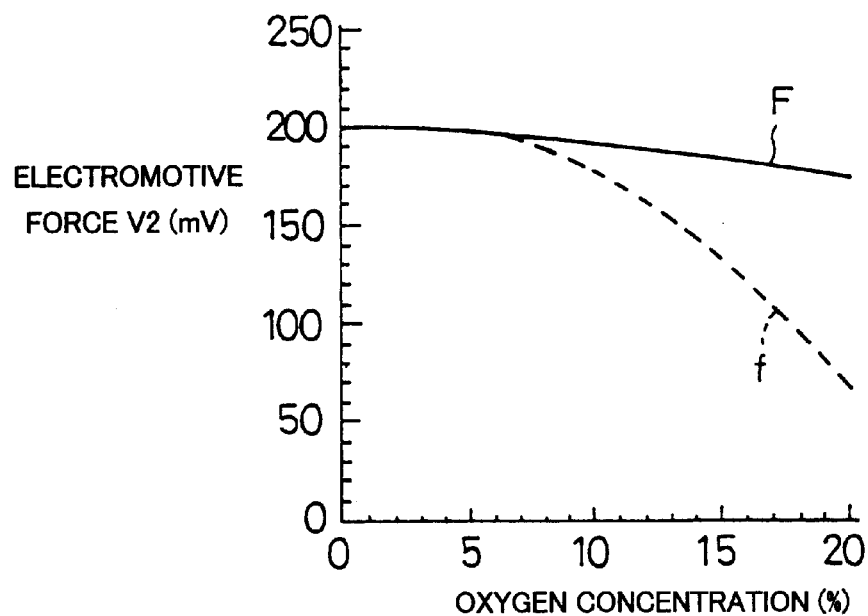
FIG. 8 shows experimental results obtained in a fourth illustrative experiment, representing characteristic curves concerning the relationship between the oxygen concentration in a measurement gas and the electromotive force V2 generated in a measuring oxygen partial pressure-detecting cell.

In the fourth illustrative experiment, observation was made for the relationship between the oxygen concentration (%) contained in the measurement gas G and the electromotive force V2 (mV) generated between the detecting electrode 102 and the reference electrode 74 of the measuring oxygen partial pressure-detecting cell 100, concerning Example 2 and Comparative Example. Experimental results obtained in the fourth illustrative experiment are shown in FIG. 8. In FIG. 8, a characteristic curve F indicated by a solid line represents an experimental result obtained in Example 2, and a characteristic curve f indicated by a broken line represents an experimental result obtained in Comparative Example.

According to the experimental results shown in FIG. 8, the characteristic curve F obtained in Example 2 shows minimized fluctuation of the electromotive force V2 owing to a small amount of $O_2$ introduced into the second chamber 62, because $O_2$ is sufficiently pumped out in the first chamber 62, as compared with the characteristic curve f obtained in Comparative Example. Therefore, the concentration of oxides contained in the measurement gas G can be highly accurately measured in the second chamber 62 without being affected by $O_2$.

Figure 9:
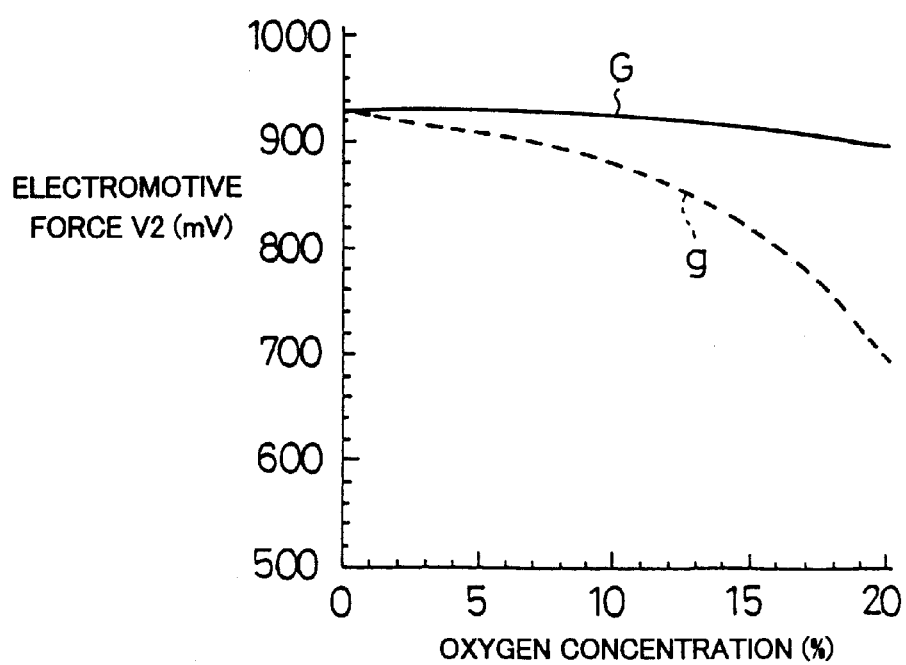
FIG. 9 shows experimental results obtained in a fifth illustrative experiment, representing characteristic curves concerning the relationship between the oxygen concentration in a measurement gas and the electromotive force V2 generated in a measuring oxygen partial pressure-detecting cell.

In the fifth illustrative experiment, Example 2 and Comparative Example were applied to sensors for measuring the amount of the inflammable gas such as CO and hydrocarbon contained in the measurement gas G, in which observation was made for the relationship between the oxygen concentration (%) contained in the measurement gas G and the electromotive force V2 (mV) generated between the detecting electrode 102 and the reference electrode 74 of the measuring oxygen partial pressure-detecting cell 100. Experimental results obtained in the fifth illustrative experiment are shown in FIG. 9. In FIG. 9, a characteristic curve G indicated by a solid line represents an experimental result obtained in Example 2, and a characteristic curve g indicated by a broken line represents an experimental result obtained in Comparative Example.

According to the experimental results shown in FIG. 9, the characteristic curve G obtained in Example 2 shows minimized fluctuation of the electromotive force V2 owing to a small amount of $O_2$ introduced into the second chamber 62, because $O_2$ is sufficiently pumped out in the first chamber 62, in the same manner as the fourth illustrative experiment described above, as compared with the characteristic curve g obtained in Comparative Example. Therefore, the concentration of oxides contained in the measurement gas G can be highly accurately measured in the second chamber 62 without being affected by $O_2$.

Next, a gas sensor 50C according to a third embodiment will be explained with reference to FIG. 10. Components or parts of the gas sensor 50C corresponding to those shown in FIG. 2 are designated by the same reference numerals, duplicate explanation of which will be omitted.

Figure 10:
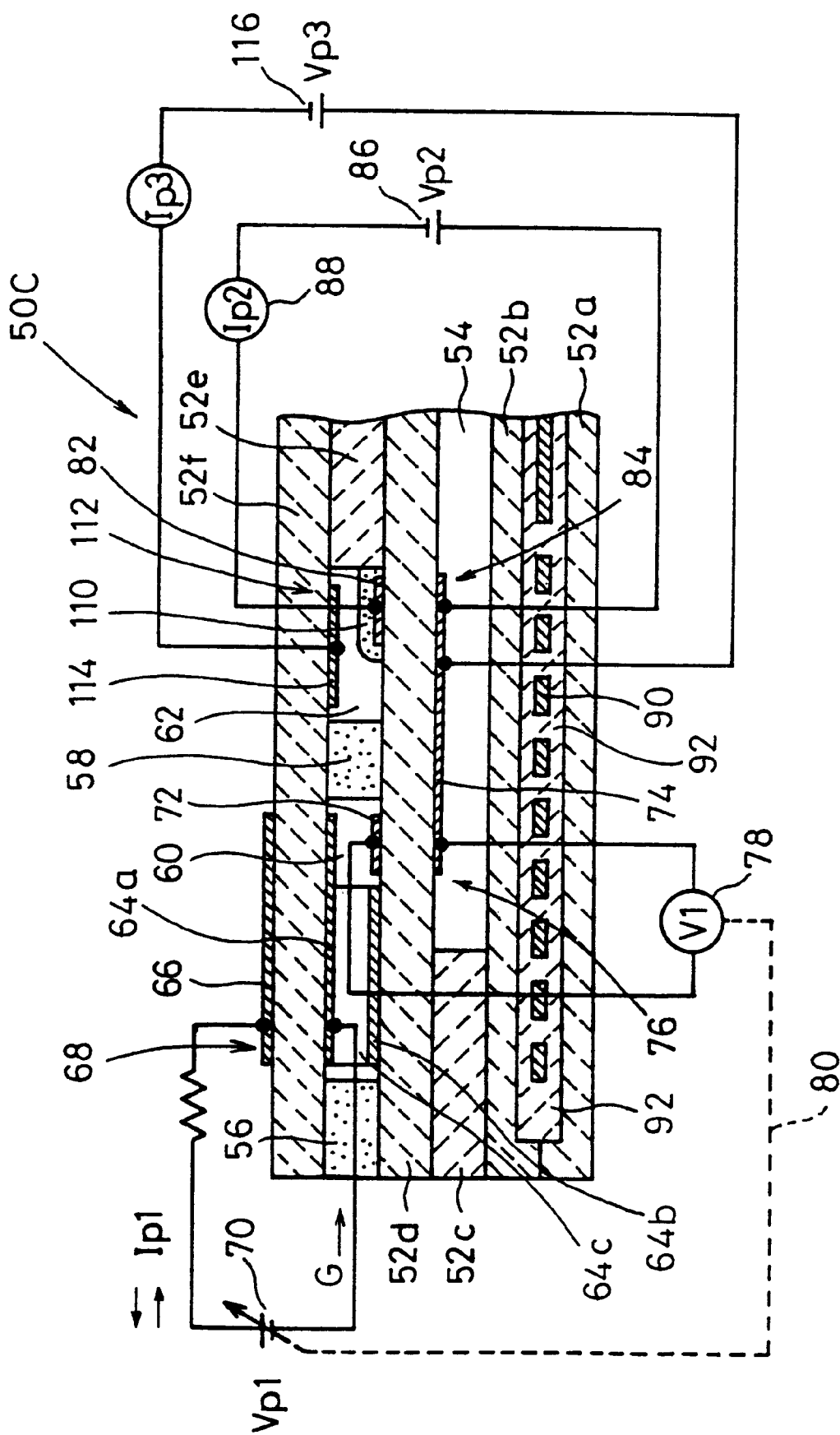
FIG. 10 shows a cross-sectional view illustrating a gas sensor according to a third embodiment.

As shown in FIG. 10, the gas sensor 50C according to the third embodiment has approximately the same structure as that of the gas sensor 50A according to the first embodiment (see FIG. 2). However, the former is different from the latter in that a porous $Al_2O_3$ layer or a porous $ZrO_2$ layer for constructing a third diffusion rate-determining section 110 is formed to cover the detecting electrode 82, and an auxiliary pumping cell 112 is provided.

The auxiliary pumping cell 112 comprises an auxiliary pumping electrode 114 composed of a porous cermet electrode having a flat and substantially rectangular shape and formed on an entire surface portion for forming the second chamber 62, of the lower surface of the second solid electrolyte layer 52f, the reference electrode 74, the second solid electrolyte layer 52f, the second spacer layer 52e, and the first solid electrolyte layer 52d.

The auxiliary pumping electrode 114 is constructed by using a material having a weak reducing ability or no reducing ability with respect to the NO components in the measurement gas, in the same manner as the inner pumping electrode 64 of the main pumping cell 68. In this embodiment, it is preferable that the auxiliary pumping electrode 114 is composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

A desired constant voltage Vp3 is applied between the auxiliary pumping electrode 114 and the reference electrode 74 of the auxiliary pumping cell 112 by the aid of an external power source 116. Thus the oxygen in the atmosphere in the second chamber 62 can be pumped out to the reference gas-introducing space 54.

Accordingly, the partial pressure of oxygen in the atmosphere in the second chamber 62 is in a situation in which the measurement gas components (NOx) are not substantially reduced or decomposed, while giving a low value of the partial pressure of oxygen at which the measurement of the amount of the objective components is not substantially affected. In this embodiment, the change in amount of oxygen introduced into the second chamber 62 is greatly reduced as compared with the change which occurs in the measurement gas G, owing to the operation of the main pumping cell 68 in the first chamber 60. Therefore, the partial pressure of oxygen in the second chamber 62 is controlled accurately and constantly.

The gas sensor 50C according to the third embodiment includes the DC power source 86. NOx flows into the measuring pumping cell 84 while being limited by the third diffusion rate-determining section 110. Under this condition, the DC power source 86 is capable of applying a voltage having a magnitude to give a limiting current for pumping to be performed for oxygen produced during decomposition in the measuring pumping cell 84.

Therefore, in the gas sensor 50C according to the third embodiment constructed as described above, the measurement gas G, which has been controlled for its partial pressure of oxygen in the second chamber 62, is introduced into the detecting electrode 82 under a predetermined diffusion resistance through the third diffusion rate-determining section 110.

When it is intended to control the partial pressure of oxygen in the atmosphere in the first chamber 60 to have a low value of the partial pressure of oxygen which does not substantially affect the measurement of NOx, by operating the main pumping cell 68, in other words, when the pumping voltage Vp1 of the variable power source 70 is adjusted by the aid of the feedback control system 80 so that the voltage V1 detected by the controlling oxygen partial pressure-detecting cell 76 is constant, if the oxygen concentration in the measurement gas G greatly changes, for example, in a range of 0 to 20%, then the respective partial pressures of oxygen in the atmosphere in the second chamber 62 and in the atmosphere in the vicinity of the detecting electrode 82 slightly change in ordinary cases. This phenomenon is caused probably because of the following reason. Namely, when the oxygen concentration in the measurement gas G increases, the distribution of the oxygen concentration occurs in the widthwise direction and the thickness direction in the first chamber 60 over the measuring electrode 72. The distribution of the oxygen concentration changes depending on the oxygen concentration in the measurement gas G.

However, in the case of the gas sensor 50C according to the third embodiment, the auxiliary pumping cell 112 is provided for the second chamber 62 so that the partial pressure of oxygen in its internal atmosphere always has a constant low value of the partial pressure of oxygen. Accordingly, even when the partial pressure of oxygen in the atmosphere introduced from the first chamber 60 into the second chamber 62 changes depending on the oxygen concentration in the measurement gas G, the partial pressure of oxygen in the atmosphere in the second chamber 62 can be always made to have a constant low value, owing to the pumping operation performed by the auxiliary pumping cell 112. As a result, the partial pressure of oxygen can be controlled to have a low value at which the measurement of NOx is not substantially affected.

NOx in the measurement gas G introduced into the detecting electrode 82 is reduced or decomposed around the detecting electrode 82. Thus, for example, a reaction of NO→½N$_2$+½O$_2$ is allowed to occur. In this process, a predetermined voltage Vp2, for example, 430 mV (700° C.) is applied between the detecting electrode 82 and the reference electrode 74 for constructing the measuring pumping cell 84, in a direction to pump out the oxygen from the second chamber 62 to the reference gas-introducing space 54.

Therefore, the pumping current Ip2 flowing through the measuring pumping cell 84 has a value which is proportional to a sum of the oxygen concentration in the atmosphere introduced into the second chamber 62, i.e., the oxygen concentration in the second chamber 62 and the oxygen concentration produced by reduction or decomposition of NOx by the aid of the detecting electrode 82.

In this embodiment, the oxygen concentration in the atmosphere in the second chamber 62 is controlled to be constant by means of the auxiliary pumping cell 112. Accordingly, the pumping current Ip2 flowing through the measuring pumping cell 84 is proportional to the NOx concentration. The NOx concentration corresponds to the amount of diffusion of NOx limited by the third diffusion rate-determining section 110. Therefore, even when the oxygen concentration in the measurement gas G greatly changes, it is possible to accurately measure the NOx concentration, based on the use of the measuring pumping cell 84 by the aid of the ammeter 88.

It is assumed, for example, that the partial pressure of oxygen in the atmosphere in the second chamber 62 controlled by the auxiliary pumping cell 112 is 0.02 ppm, and the concentration of NO as the NOx component in the measurement gas is 100 ppm. The pumping current Ip2 flows in an amount corresponding to a sum (=50.02 ppm) of an oxygen concentration of 50 ppm produced by reduction or decomposition of NO and the oxygen concentration of 0.02 ppm in the atmosphere in the second chamber 62. Therefore, almost all of the pumping current value Ip2 obtained by operating the measuring pumping cell 84 represents the amount brought about by the reduction or decomposition of NO. Accordingly, the obtained result does not depend on the oxygen concentration in the measurement gas.

Next, a gas sensor 50D according to a fourth embodiment will be explained with reference to FIG. 11. Components or parts of the gas sensor 50D corresponding to those shown in FIGS. 7 and 10 are designated by the same reference numerals, duplicate explanation of which will be omitted.

Figure 11:
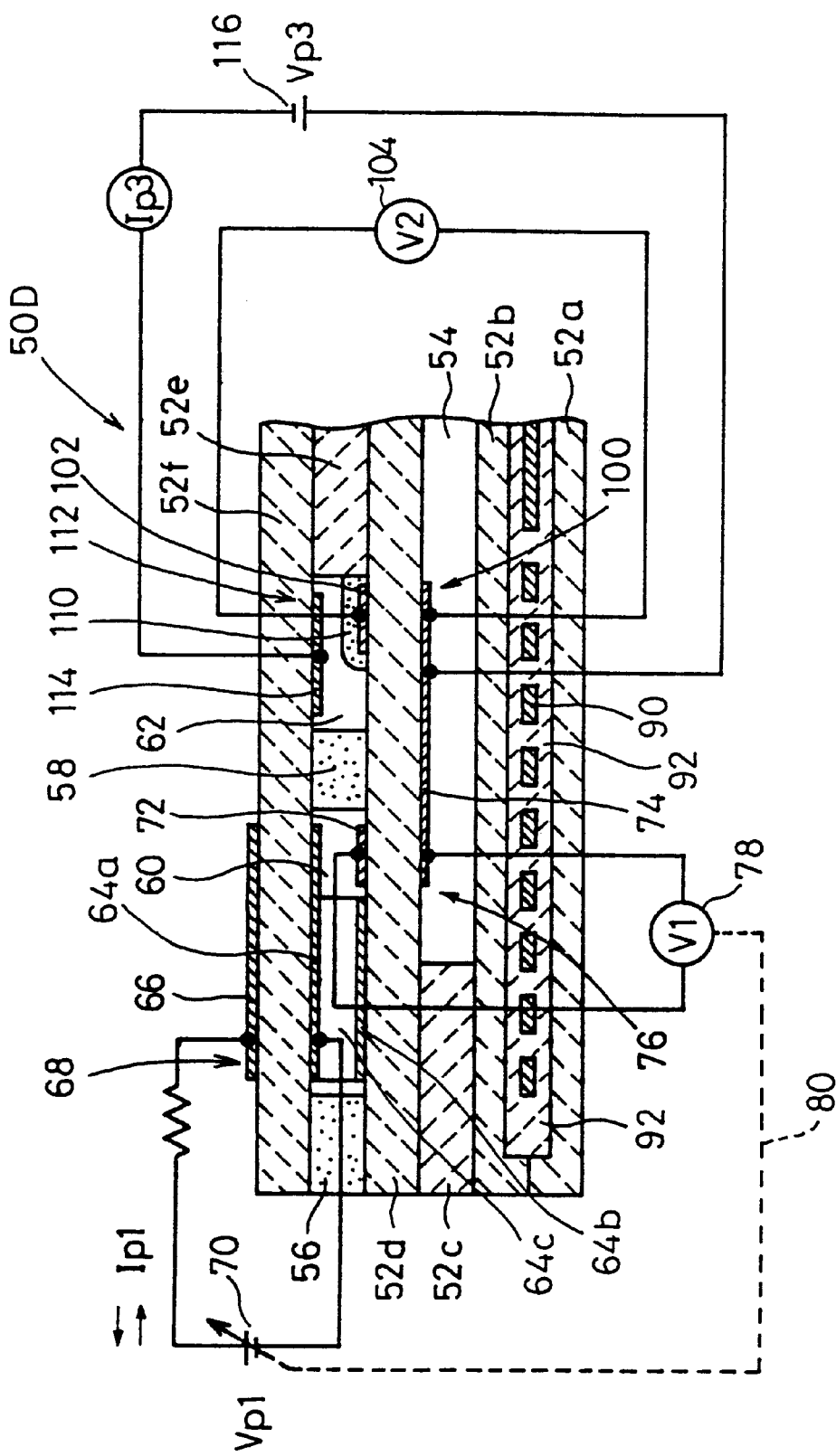
FIG. 11 shows a cross-sectional view illustrating a gas sensor according to a fourth embodiment.

As shown in FIG. 11, the gas sensor 50D according to the fourth embodiment has approximately the same structure as that of the gas sensor 50B according to the second embodiment (see FIG. 7). However, the former is different from the latter in that a porous Al$_2$O$_3$ layer or a porous ZrO$_2$ layer for constructing a third diffusion rate-determining section 110 is formed to cover the detecting electrode 102 of the measuring oxygen partial pressure-detecting cell 100, and an auxiliary pumping cell 112 is provided, in the same manner as the gas sensor 50C according to the third embodiment (see FIG. 10).

In this embodiment, the partial pressure of oxygen in the atmosphere in the second chamber 62 is in a situation in which the measurement gas components (NOx) are not substantially reduced or decomposed, while giving a low value of the partial pressure of oxygen at which the measurement of the amount of the objective components is not substantially affected, in the same manner as the gas sensor 50C according to the third embodiment. The change in amount of oxygen introduced into the second chamber 62 is greatly reduced as compared with the change which occurs in the measurement gas G, owing to the operation of the main pumping cell 68 in the first chamber 60. Therefore, the partial pressure of oxygen in the second chamber 62 is controlled accurately and constantly.

Therefore, even when the oxygen concentration in the measurement gas G greatly changes, it is possible to accurately measure the NOx concentration, based on the use of the measuring oxygen partial pressure-detecting cell 100 by the aid of the voltmeter 104.

Figure 12:
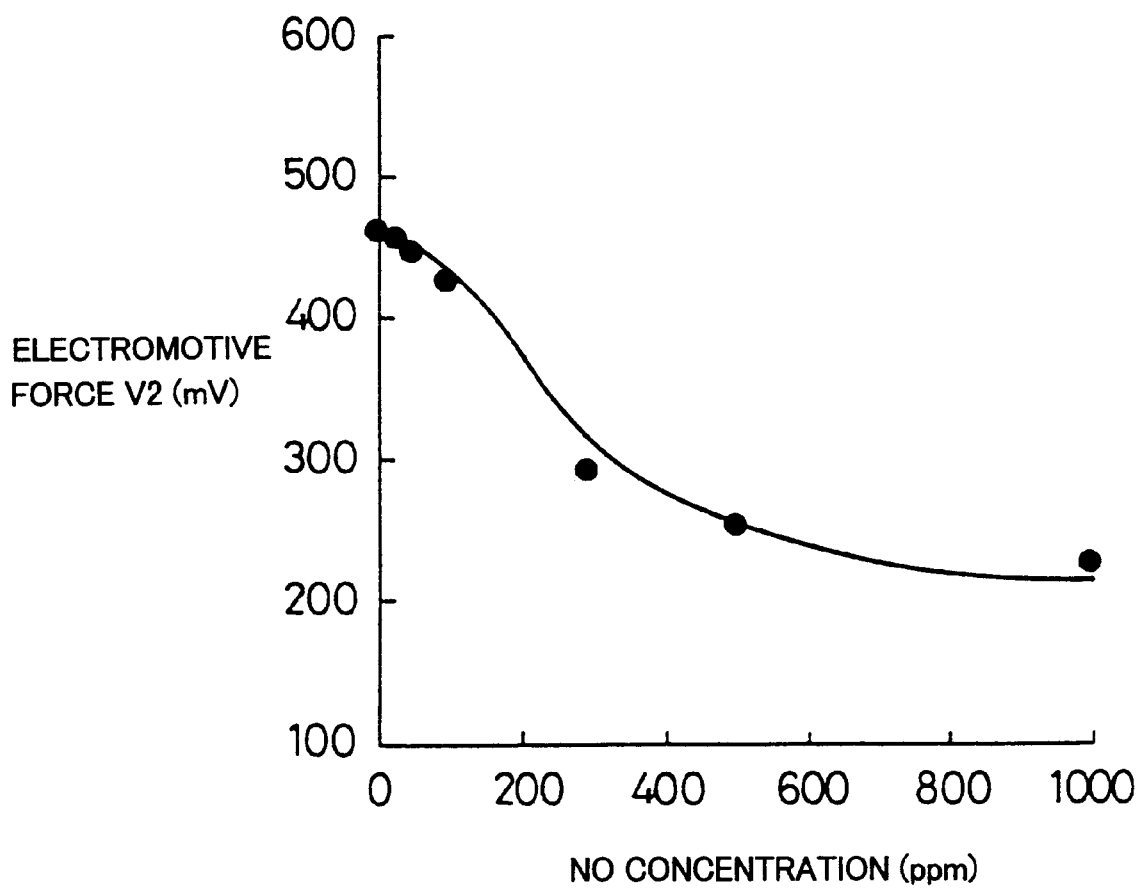
FIG. 12 shows a characteristic of the gas sensor according to the fourth embodiment, illustrating the change in electromotive force generated in a measuring oxygen partial pressure-detecting cell depending on the change in NO concentration.

Now, the principle of detection performed by the gas sensor 50D according to the fourth embodiment will be explained with reference to FIG. 12 illustrating a characteristic of the gas sensor 50D.

At first, when the NO concentration in the external space is 0 ppm, the pumping voltage Vp1 of the main pumping cell 68 is controlled so that the partial pressure of oxygen in the atmosphere in the first chamber 60 is maintained to be $1.3\times10^{-7}$ atm, i.e., to give a value of the electromotive force V1=about 300 mV.

Next, the set voltage Vp3 applied to the auxiliary pumping cell 112 is set to be 460 mV. The partial pressure of oxygen in the second chamber 62 is controlled to be $6.1\times10^{-11}$ atm owing to the operation performed by the auxiliary pumping cell 112. As a result, the electromotive force V2 between the detecting electrode 102 and the reference electrode 74 of the measuring oxygen partial pressure-detecting cell 100 is about 460 mV.

In this case, the inflammable gas components are oxidized in the first chamber 60, and the sensitivity to NOx is not affected thereby, because the partial pressure of oxygen in the first chamber 60 is $1.3\times10^{-7}$ atm, regardless of the fact that the partial pressure of oxygen in the second chamber 62 is $6.1\times10^{-11}$ atm.

If the NO concentration in the external space gradually increases, the reduction or decomposition reaction of NO is caused on the detecting electrode 102, because the detecting electrode 102 also functions as a NOx-reducing catalyst in the same manner as the detecting electrode 82 of the measuring pumping cell 84 described above (see FIG. 2). As a result, the oxygen concentration in the atmosphere around the detecting electrode 102 is increased. Accordingly, the electromotive force V2 generated between the detecting electrode 102 and the reference electrode 74 is gradually decreased. With reference to FIG. 12 illustrating the characteristic of the gas sensor 50D, for example, when the NO concentration increases to 300 ppm, 500 ppm, and 1000 ppm, the electromotive force V2 detected by the voltmeter 104 is gradually decreased to 300 mV, 250 mV, and 220 mV respectively.

The degree of the decrease in electromotive force V2 represents the NO concentration. Namely, the electromotive force V2, which is outputted from the measuring oxygen partial pressure-detecting cell 100 constructed by the detecting electrode 102, the reference electrode 74, and the first solid electrolyte layer 52d, represents the NO concentration in the measurement gas G.

Now, an illustrative experiment (referred to as "sixth illustrative experiment" for convenience) will be described. The fifth illustrative experiment was performed by providing Example 3 and Comparative Example. Example 3 was based on the use of a system constructed in the same manner as the gas sensor 50D according to the fourth embodiment including the inner pumping electrodes 64a to 64d formed on the inner wall surfaces of the first chamber 60. Comparative Example was based on the use of a system constructed by providing an auxiliary pumping cell 112 for the gas sensor concerning the conventional technique as shown in FIG. 14. In the sixth illustrative experiment, observation was made for the change in electromotive force V2 generated in the measuring oxygen partial pressure-detecting cell 100, obtained by changing the oxygen concentration in a range of 0 to 20% in a measurement gas G comprising basic gas components based on an $N_2$—$H_2O$ system. The NO component was not contained in the measurement gas G, because it was intended to correctly measure the way of change in electromotive force V2, to be obtained by changing only the oxygen concentration in the measurement gas G.

In Example 3, the pumping voltage Vp1 of the main pumping cell 68 (equivalent to the electromotive force V1) was 300 mV, and the auxiliary pumping voltage Vp3 of the auxiliary pumping cell 112 was 460 mV.

Figure 13:
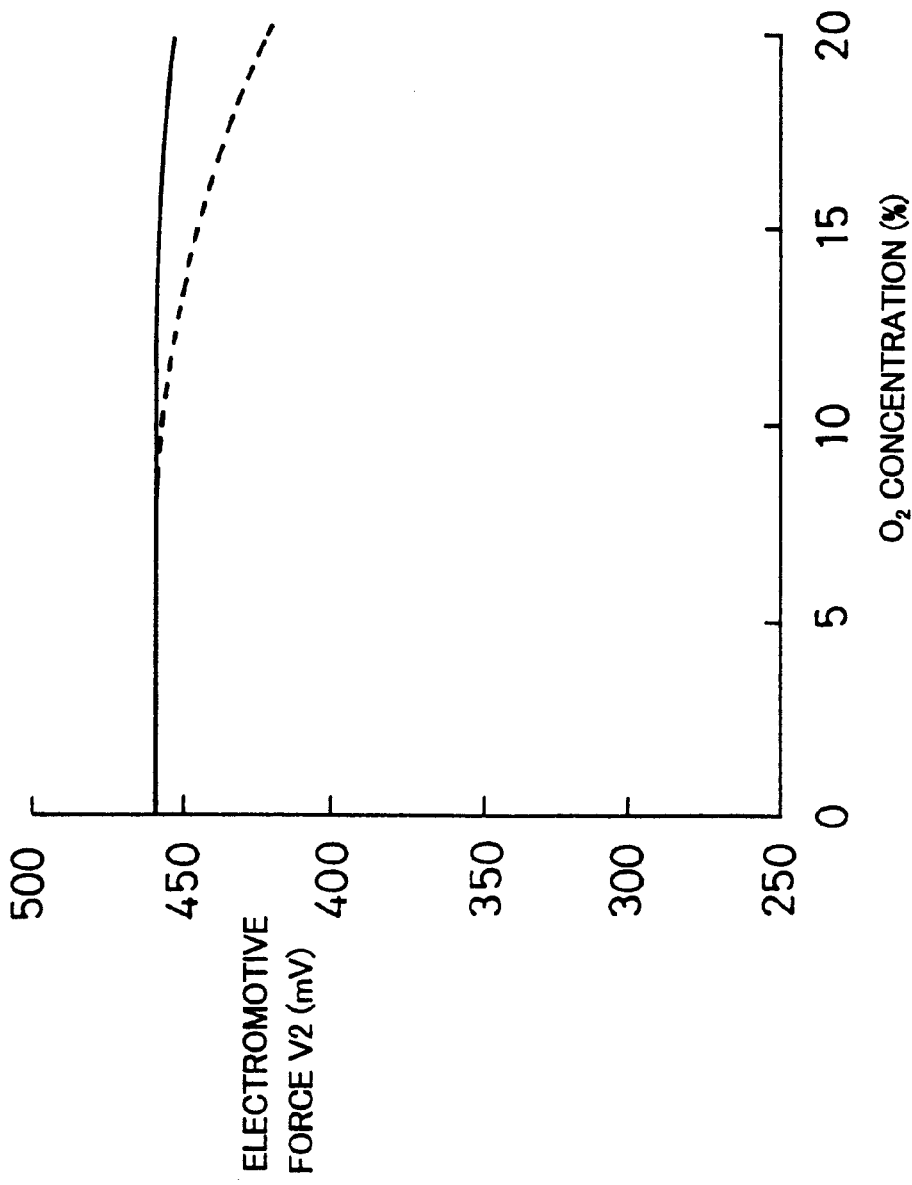
FIG. 13 shows experimental results obtained in a sixth illustrative experiment, representing characteristic curves concerning the relationship between the oxygen concentration in a measurement gas and the electromotive force V2 generated in a measuring oxygen partial pressure-detecting cell.

Experimental results obtained in the sixth illustrative experiment are shown in FIG. 13. In FIG. 13, a characteristic curve indicated by a solid line represents an experimental result obtained in Example 3, and a characteristic curve indicated by a broken line represents an experimental result obtained in Comparative Example.

As clarified from the experimental results shown in FIG. 13, the electromotive force V2 decreases in Comparative Example, as the oxygen concentration in the measurement gas G becomes high. For example, when the oxygen concentration is 0%, the electromotive force is 460 mV. However, when the oxygen concentration is 20%, the electromotive force is 425 mV.

On the contrary, Example 3 enjoys the synergistic effect of the pumping operation performed by the auxiliary pumping cell 112 and the formation of the inner pumping electrodes 64a to 64d of the main pumping cell 68, arranged on the inner wall surfaces of the first chamber 60. Namely, it is understood that even when the oxygen concentration in the measurement gas G changes in a range of 0 to 20%, the electromotive force V2 generated in the measuring oxygen partial pressure-detecting cell 100 scarcely changes, and the $O_2$-dependency of the electromotive force V2 is extremely minimized.

Accordingly, when the measurement gas G contains the NO component, the electromotive force V2 corresponding to an amount of NO is generated between the detecting electrode 102 and the reference electrode 74 for constructing the measuring oxygen partial pressure-detecting cell 100. The amount of NO can be correctly determined by detecting the electromotive force V2.

The gas sensors 50C, 50D according to the third and fourth embodiments have been illustrated for the case in which the auxiliary pumping electrode 114 for constructing the auxiliary pumping cell 112 is formed only on the upper surface portion of the second chamber 62, respectively. Alternatively, the auxiliary pumping electrode 114 may be formed in a continuous manner over the inner wall surfaces of the second chamber 62, in the same manner as the inner pumping electrodes 64a to 64d for constructing the main pumping cell 68. In such an embodiment, it is possible to efficiently remove the excessive $O_2$ component introduced into the second chamber 62.

The gas sensors 50C, 50D according to the third and fourth embodiments can be also applied to a sensor for highly accurately measuring the amount of inflammable gases such as CO and hydrocarbon contained in the measurement gas G, in the same manner as the gas sensors 50A, 50B according to the first and second embodiment.

It is a matter of course that the gas sensor according to this invention is not limited to the embodiments described above, which can be constructed in other various forms without deviating from the gist or essential characteristics of this invention.

What is claimed is:

1. A gas sensor comprising:

a main pumping means including inner and outer pumping electrodes arranged on inner and outer surfaces of a substrate composed of an oxygen ion-conductive solid electrolyte, for performing a pumping process for oxygen contained in a measurement gas introduced from external space, on the basis of a control voltage applied between said inner and outer pumping electrodes; and an electric signal-generating conversion means including inner and outer detecting electrodes arranged on inner and outer surfaces of a substrate composed of an oxygen ion-conductive solid electrolyte, for decomposing a predetermined gas component contained in said measurement gas after being subjected to said pumping process performed by said main pumping means, by the aid of a catalytic action and/or electrolysis to provide, by conversion, an electric signal corresponding to an amount of oxygen produced by said decomposition, wherein:

said inner pumping electrode is arranged on at least upper, lower, and two side surfaces of a process space processed by said main pumping means; and said predetermined gas component contained in said measurement gas is measured on the basis of said electric signal supplied from said electric signal-generating conversion means.

2. The gas sensor according to claim 1, wherein said electric signal-generating conversion means comprises:

a measuring pumping means including said inner and outer detecting electrodes arranged on said inner and outer surfaces of said substrate composed of an oxygen ion-conductive solid electrolyte, for decomposing said predetermined gas component contained in said measurement gas after being subjected to said pumping process performed by said main pumping means, by the aid of said catalytic action and/or electrolysis, and performing a pumping process for said oxygen produced by said decomposition on the basis of a measuring voltage applied between said inner and outer detecting electrodes; and a current-detecting means for detecting a pumping current generated corresponding to an amount of said oxygen subjected to said pumping process performed by said measuring pumping means, wherein:

said predetermined gas component in said measurement gas is measured on the basis of said pumping current detected by said current-detecting means.

3. The gas sensor according to claim 1, wherein said electric signal-generating conversion means comprises:

a concentration-detecting means including said inner and outer detecting electrodes arranged on said inner and outer surfaces of said substrate composed of an oxygen ion-conductive solid electrolyte, for decomposing said predetermined gas component contained in said measurement gas after being subjected to said pumping process performed by said main pumping means, by the aid of said catalytic action and/or electrolysis, and generating an electromotive force corresponding to a difference between said amount of oxygen produced by said decomposition and an amount of oxygen contained in a gas existing on a side of said outer detecting electrode; and a voltage-detecting means for detecting said electromotive force generated by said concentration-detecting means, wherein:

said predetermined gas component in said measurement gas is measured on the basis of said electromotive force detected by said voltage-detecting means.

4. The gas sensor according to claim 1, wherein said predetermined gas component is an oxide.

5. The gas sensor according to claim 4, wherein said oxide is a nitrogen oxide.

6. The gas sensor according to claim 1, wherein said predetermined gas component is an inflammable gas, and said main pumping means is operated so that an atmosphere in said process space processed by said main pumping means is set to contain a predetermined amount of oxygen at which said inflammable gas does not burn.

7. The gas sensor according to claim 6, wherein said inflammable gas is hydrogen, carbon monoxide, or hydrocarbon.

8. The gas sensor according to claim 1, further comprising a plurality of process spaces each having a diffusion rate-determining section for giving a predetermined diffusion resistance to said measurement gas, for measuring different types of oxides or inflammable gases respectively.

9. The gas sensor according to claim 1, wherein said inner pumping electrodes are composed of an inactive material having a low catalytic activity on oxides.

10. The gas sensor according to claim 1, wherein said control voltage supplied to said main pumping means is a voltage at which said partial pressure of oxygen in said process space processed by said main pumping means is not less than $2 \times 10^{-8}$ atm.

11. The gas sensor according to claim 1, further comprising an auxiliary pumping means including inner and outer auxiliary pumping electrodes arranged on the inner and outer surfaces of a substrate composed of an oxygen ion-conductive solid electrolyte, for performing a pumping process for oxygen contained in said measurement gas in a second process space after being subjected to said pumping process performed by said main pumping means, on the basis of an auxiliary pumping voltage applied between said inner and outer auxiliary pumping electrodes.

12. The gas sensor according to claim 11, wherein said inner auxiliary pumping electrode is arranged at least on upper and lower surfaces of said second process space.

13. The gas sensor according to claim 1, further comprising:

a concentration-detecting means including an inner measuring electrode exposed to said process space processed by said main pumping means and an outer measuring electrode exposed to a reference gas-introducing space, for measuring an electromotive force of an oxygen concentration cell generated between said inner and outer measuring electrodes, as a partial pressure of oxygen in said process space processed by said main pumping means; and a main pumping control means for adjusting a level of said control voltage so that said electromotive force of said oxygen concentration cell detected by said concentration-measuring means has a predetermined value.

\* \* \* \* \*